(12) United States Patent
Jones et al.

(10) Patent No.: US 10,166,199 B2
(45) Date of Patent: Jan. 1, 2019

(54) TRANSDERMAL PATCH COMPRISING A ROPIVACAINE FORMULATION

(71) Applicant: BUZZZ PHARMACEUTICALS LIMITED, Raheny, Dublin (IE)

(72) Inventors: Chris Jones, Cardiff (GB); Darren Green, Cardiff (GB)

(73) Assignee: Buzzz Pharmaceuticals Limited, Dublin (IE)

( * ) Notice: Subject to any disclaimer, the term of this patent is extended or adjusted under 35 U.S.C. 154(b) by 0 days.

(21) Appl. No.: 15/027,905

(22) PCT Filed: Oct. 7, 2014

(86) PCT No.: PCT/EP2014/071437
§ 371 (c)(1),
(2) Date: Apr. 7, 2016

(87) PCT Pub. No.: WO2015/052183
PCT Pub. Date: Apr. 16, 2015

(65) Prior Publication Data
US 2016/0235689 A1    Aug. 18, 2016

(30) Foreign Application Priority Data

Oct. 7, 2013  (EP) ........................................ 1317718

(51) Int. Cl.
*A61K 9/70* (2006.01)
*A61K 47/10* (2017.01)
(Continued)

(52) U.S. Cl.
CPC .......... *A61K 9/7061* (2013.01); *A61K 31/445* (2013.01); *A61K 31/485* (2013.01);
(Continued)

(58) Field of Classification Search
None
See application file for complete search history.

(56) References Cited

U.S. PATENT DOCUMENTS

| | | | |
|---|---|---|---|
| 4,956,171 A * | 9/1990 | Chang ................. | A61K 9/0014 424/448 |
| 9,295,655 B2 * | 3/2016 | Choi .................... | A61K 9/7053 |

(Continued)

FOREIGN PATENT DOCUMENTS

| | | |
|---|---|---|
| EP | 1661560 | 5/2006 |
| EP | 1964552 | 9/2008 |

(Continued)

OTHER PUBLICATIONS

Merriam Webster definition of oil (obtained online May 25, 2017).*

(Continued)

*Primary Examiner* — Robert A Wax
*Assistant Examiner* — Melissa S Mercier
(74) *Attorney, Agent, or Firm* — Barnes & Thornburg, LLP

(57) ABSTRACT

The present invention relates to a transdermal patch comprising a pharmaceutical formulation, the formulation comprising ropivacaine or an opioid, a pharmaceutically-acceptable adhesive and optionally one or more excipients selected from the group consisting of carrier oils, penetration enhancers and hydrophilic materials. The present invention also relates to methods of preparation of such a pharmaceutical formulation, as well as the use of such a transdermal patch in the treatment of pain (e.g. nociceptive and/or neuropathic pain).

19 Claims, 13 Drawing Sheets

Figure 1:
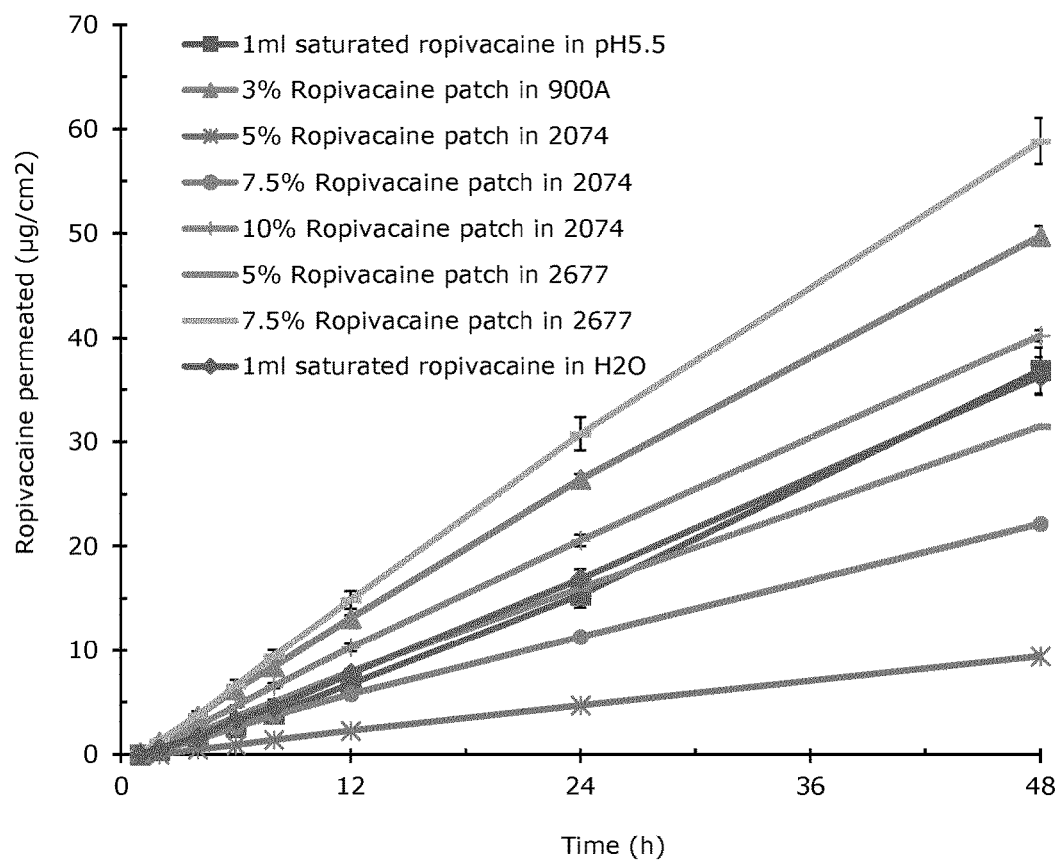

(51) Int. Cl.
  *A61K 31/445* (2006.01)
  *A61K 47/14* (2017.01)
  *A61K 31/485* (2006.01)
  *A61K 47/22* (2006.01)

(52) U.S. Cl.
  CPC .............. *A61K 47/10* (2013.01); *A61K 47/14* (2013.01); *A61K 47/22* (2013.01)

(56) References Cited

U.S. PATENT DOCUMENTS

| | | |
|---|---|---|
| 2002/0197284 A1 | 12/2002 | Luo et al. |
| 2004/0096491 A1 | 5/2004 | Tateishi et al. |
| 2005/0087195 A1 | 4/2005 | Huang |
| 2005/0276842 A1 | 12/2005 | Zhang et al. |
| 2007/0059351 A1 | 3/2007 | Murrell et al. |
| 2007/0189978 A1* | 8/2007 | Zhang ............... A61K 9/0014 424/45 |
| 2010/0008991 A1 | 1/2010 | Mantelle |
| 2011/0104093 A1* | 5/2011 | McLaughlin ........ A61K 8/60 424/70.11 |
| 2013/0072884 A1* | 3/2013 | Hamlin ............... A61K 9/703 604/304 |

FOREIGN PATENT DOCUMENTS

| | | |
|---|---|---|
| EP | 2177217 A1 | 4/2010 |
| EP | 2687205 | 1/2014 |
| EP | 2759294 | 7/2014 |
| WO | WO2005123046 | 12/2005 |
| WO | WO2007070679 | 6/2007 |
| WO | WO2007100910 | 9/2007 |
| WO | WO2011005853 | 1/2011 |
| WO | WO2011/121082 A1 | 10/2011 |
| WO | WO2016009063 A1 | 1/2016 |

OTHER PUBLICATIONS

PCT Search Report and Written Opinion for PCT/EP2014/071437, completed Nov. 19, 2014.
GB Search Report for GB1317718.3, completed Apr. 8, 2014.
Power, I., "An Update on Analgesics;" 2011; British Journal of Anaesthesia; 107, (1); pp. 19-24.
Cilurzo, F., "Adhesive properties: a critical issue in transdermal patch development," 2012, Expert Opin. Drug Deliv. 9(1):33-45.
Roy et al. "Transdermal delivery of buprenorphine through cadaver skin" Journal of Pharmaceutical Sciences, vol. 83, No. 2, 1994, pp. 126-130.
Taghizadeh et al. "Preparation and In Vitro Evaluation of a New Fentanyl Patch Based on Acrylic/Silicone Pressure-Sensitive Adhesive Blends" Drug Development and Industrial Pharmacy, vol. 35, No. 4, 2009, pp. 487-498.
Liao et al. "In Vitro Skin Permeation of Buprenorphine Transdermal Patch" Journal of Food and Drug Analysis, vol. 16, No. 6, 2008, pp. 8-15.
Roy et al. "Controlled transdermal delivery of fentanyl: Characterizations of pressure-sensitive adhesives for matrix patch design" Journal of Pharmaceutical Sciences, vol. 85, No. 5, 1996, pp. 491-495.

* cited by examiner

TRANSDERMAL PATCH COMPRISING A ROPIVACAINE FORMULATION

CROSS-REFERENCE TO RELATED APPLICATIONS

This application is a U.S. national phase of PCT/EP2014/071437, filed on Oct. 7, 2014, which claims priority to European Patent Application No. 1317718.3, filed on Oct. 7, 2013. The disclosures of both European Patent Application No. 1317718.3 and PCT Application No. PCT/EP2014/071437 are hereby incorporated herein by reference in their entireties.

FIELD OF THE INVENTION

The present invention relates to a novel formulation. More specifically, the present invention relates to a novel anaesthetic or analgesic formulation suitable for transdermal administration. Such formulations are suitable for the topical treatment of neuropathic and/or nociceptive pain. The present invention also relates to processes for the preparation of the formulations defined herein, as well as to the use of these formulations for the topical treatment of neuropathic and/or nociceptive pain.

BACKGROUND OF THE INVENTION

Nociceptive pain is pain generated from nociceptors responding to stimuli by sending nerve signals to the spinal cord and brain. Such signals may be indicative of tissue irritation, impending injury, or actual injury, and are often characterized as aching and/or direct pains. Examples of conditions associated with nociceptive pain include bone fractures, burns, bumps, bruises, inflammation (from an infection or arthritic disorder), arthralgia, general myalgia and more specific myalgia caused by symptoms categorized generally as amplified musculoskeletal pain (AMP) syndrome.

Neuropathic pain is pain caused by damage or disease that affects the somatosensory system. Neuropathic pain is the result of an injury or malfunction in the peripheral or central nervous system. The pain is often triggered by an injury, but it is not necessary for such an injury to involve actual damage to the central nervous system. Nerves can be infiltrated or compressed by tumours, strangulated by scar tissue, or inflamed by infection. The pain is typically characterized by burning, lancinating, coldness or so-called pins-and-needles-type sensations. Persistent allodynia—pain resulting from a non-painful stimulus such as a light touch—is also a common characteristic of neuropathic pain. The pain itself may have continuous and/or episodic (paroxysmal) components, the having electric shock-like qualities. The pain may persist for months or years beyond the apparent healing of any damaged tissue. In these scenarios, such pain signals no longer represent an alarm about ongoing or impending injury, rather it is the alarm system itself that is malfunctioning. Common causes of painful peripheral neuropathies are herpes zoster, infection, HIV-related neuropathies, nutritional deficiencies, toxins, remote manifestations of malignancies, immune mediated disorders and physical trauma to a nerve trunk. Neuropathic pain is also common in cases of cancer, either as a direct result of a cancer on peripheral nerves (for example through compression by a tumour), or as a side effect of chemotherapy radiation, injury or surgery.

In certain conditions, the pain may be caused by a complex mixture of nociceptive and neuropathic factors. For example, myofascial pain is understood to result from nociceptive input from muscles. It is, however, plausible that such abnormal muscle activity is itself the result of neuropathic conditions.

In both neuropathic and nociceptive disease types, neurons become unusually sensitive and develop spontaneous activity, abnormal excitability, and a heightened sensitivity to chemical, thermal and mechanical stimuli. This phenomenon is known as "peripheral sensitization". Localized delivery of anaesthetic can afford a method of desensitizing the aberrant stimuli.

Lidocaine (often referred to as lignocaine) is widely used as a local anaesthetic, and is commercially available in both an injectable form and as a transdermal patch. When compared with a systemic dose, transdermal delivery of local anaesthetics provides prolonged anaesthesia at the target site for pain suppression, and involves reduced plasma levels, hence a reduced potential toxicity.

However, in spite of the widespread use of lignocaine transdermal patches, there remains a need for improved transdermal anaesthetic formulations.

In addition, there remains a need for improved analgesic transdermal patch formulations to provide analgesia, in particular improved patches for the delivery of opioid analgesics.

There is also a need for transdermal formulations having good skin penetration properties. Moreover, there is a need for transdermal formulations of anaesthetic or analgesic agents that exhibit improved drug potency and having a longer duration of action for reducing the occurrence of breakthrough pain.

Aspects of the invention were devised with the foregoing in mind.

SUMMARY OF THE INVENTION

The present invention provides a novel pharmaceutical formulation suitable for topical application for the treatment of pain, for example nociceptive and/or neuropathic pain.

Thus, according to a first aspect of the invention, there is provided a transdermal patch comprising a pharmaceutical formulation, said formulation comprising ropivacaine or an opioid and a pharmaceutically-acceptable adhesive, and wherein said formulation has an in vitro permeation rate greater than 1.8 µg cm$^{-2}$ h$^{-1}$.

In another aspect, the present invention provides a transdermal patch comprising a pharmaceutical formulation, said formulation comprising:
(i) ropivacaine or an opioid,
(ii) a pharmaceutically-acceptable adhesive, and optionally
(iii) one or more of either a penetration enhancer, a hydrophilic material, and a carrier oil having a ropivacaine or an opioid solubility of greater than or equal to 1.5% (w/w).

In another aspect, the present invention provides a pharmaceutical formulation suitable for inclusion into a transdermal patch as herein defined, said formulation comprising ropivacaine or an opioid and a pharmaceutically-acceptable adhesive, and wherein said formulation has an in vitro human skin permeation rate greater than 1.8 µg cm$^{-2}$ h$^{-1}$.

In another aspect, the present invention provides a pharmaceutical formulation comprising:
(i) ropivacaine or an opioid,
(ii) a pharmaceutically-acceptable adhesive, and optionally (iii) one or more of either a penetration enhancer, a hydrophilic material, and a carrier oil having a ropivacaine or an opioid solubility of greater than or equal to 1.5% (w/w).

wherein said formulation is suitable for inclusion into a transdermal patch as herein defined.

In another aspect, the present invention provides a pharmaceutical formulation or transdermal patch as herein defined for use as a medicament.

In another aspect, the present invention provides a pharmaceutical formulation or transdermal patch as herein defined for use in the treatment of pain (e.g. neuropathic and/or nociceptive pain).

In another aspect, the present invention provides a method of treating pain (e.g. neuropathic and/or nociceptive pain), said method comprising topically administering to a human or animal subject in need of such treatment a therapeutically effective amount of a pharmaceutical formulation as defined herein, or applying a transdermal patch as herein defined.

In another aspect, the present invention provides a method of preparing a pharmaceutical formulation as defined herein, said method comprising mixing:
(i) ropivacaine or an opioid,
(ii) an adhesive as defined herein, and optionally
(iii) one or more of a penetration enhancer as defined herein, a hydrophilic material as defined herein and a carrier oil as herein defined and having a ropivacaine or an opioid solubility of greater than or equal to 1.5% (w/w).

DETAILED DESCRIPTION OF THE INVENTION

Ropivacaine

Ropivacaine, chemical name (2S)—N-(2,6-dimethylphenyl)-1-propyl-2-piperidinecarboxamide and having the structure shown below, is an aminoamide containing an asymmetric carbon atom, and is produced as the single S enantiomer for clinical use as local anaesthetic.

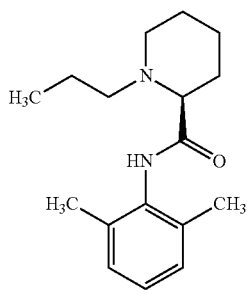 [SMILES: CCCN1CCCC[C@H]1C(=O)Nc1c(C)cccc1C]

Studies focussing on the use of local anaesthetic during cataract surgery have demonstrated that dose-for-dose, ropivacaine may be as much as four times as potent as lidocaine anaesthetics. In this study, the use of ropivacaine was preferred to lidocaine due to its longer half life, which contributed to a reduction in levels of breakthrough pain.

In view of the above advantages, ropivacaine presents a suitable candidate for inclusion into a transdermal patch for the treatment of pain, such as nociceptive and neuropathic pain. In theory, such advantages would allow for a transdermal patch having improved drug potency and enhanced drug persistence characteristics.

However, in spite of the advantages discussed above, ropivacaine saturated $H_2O$ has been demonstrated to be exhibit significantly poorer skin permeation characteristics than lidocaine saturated $H_2O$ (see FIG. 6), thereby presenting a considerable barrier to transdermal patch development.

When used in conjunction with the present invention, ropivacaine may be present in its free base form, or as a salt. Suitably, when used as part of the pharmaceutical formulation described herein, ropivacaine is present in its free base form, since it is commonly understood that the skin is typically more permeable to uncharged lipophilic permeants, as opposed to charged species. The free base form would also be expected to be more soluble in typical pharmaceutical adhesives than would a salt form (e.g. ropivacaine HCl).

The amount of ropivacaine present in the pharmaceutical formulation of the present invention will depend on how soluble it is in the pharmaceutically-acceptable adhesive and excipients present. Typically, the ropivacaine will present at an amount of 3-20% w/w.

In one embodiment, the amount of ropivacaine is between 3 and 10% w/w.

Suitably, the amount of ropivacaine is between 6 and 8% w/w.

Opioid Analgesiscs

The transdermal patches of the present invention may comprise an opioid analgesic. Any suitable opioid analgesic may be used.

In an embodiment, the opioid analgesic is selected from morphine, codeine, thebaine, diacetylmorphine (morphine diacetate; heroin), nicomorphine (morphine dinicotinate), dipropanoylmorphine (morphine dipropionate), desomorphine, acetylpropionylmorphine, dibenzoylmorphine, diacetyldihydromorphine, hydromorphone, hydrocodone, oxycodone, oxymorphone, ethylmorphine and buprenorphine, fentanyl, pethidine, levorphanol, methadone, tramadol and dextropropoxyphene.

The amount of opioid present in the pharmaceutical formulation of the present invention will depend on how soluble it is in the pharmaceutically-acceptable adhesive and excipients present. Typically, the opioid will present at an amount of 3-20% w/w.

In one embodiment, the amount of opioid is between 3 and 10% w/w.

Suitably, the amount of opioid is between 6 and 8% w/w.

Transdermal Patch

Despite the poor in vitro skin penetration observed with a saturated solution of ropivacaine when compared to a saturated solution of lidocaine (see FIG. 6), it has surprisingly been found that it is possible to prepare a transdermal delivery system for ropivacaine.

The transdermal patches of the present invention are prepared by casting a wet pharmaceutical formulation layer as described herein at a known thickness onto a suitable release liner. In its simplest form, the pharmaceutical formulation may comprise ropivacaine or an opioid and a pharmaceutically-acceptable adhesive. The pharmaceutical formulation may additionally comprise one or more additional excipients, including a carrier oil, penetration enhancers and hydrophilic materials. Typically, the pharmaceutical formulation are cast at a wet thickness of between about 240 μm to about 550 μm, to provide a dry thickness of between about 45 μm and about 95 μm, suitably between about 80 μm and about 85 μm. After casting, the layer is dried, and then laminated with a backing membrane. A suitable container or closure system may be used protect the transdermal patch during transportation and storage.

Suitable backing membranes may be occlusive or non-occlusive. Where a non-occlusive backing membrane is used, it is desirable to use a fully occlusive container or closure system to prevent degradation of the cast pharmaceutical formulation layer prior to use. The backing membrane may be of any thickness, but is suitably between about 10 to 260 μm thick. Suitable materials include, but are not limited to, synthetic polymers including, for example, polyesters, polycarbonates, polyimides, polyethylene, poly(ethylene terphthalate), polypropylene, polyurethanes and polyvinylchlorides. The backing membrane may also be a laminate comprising additional layers that may include vapour deposited metal, such as aluminium, additional synthetic polymers, and other materials, to enable a heat seal, such as EVA copolymer. Suitably, the backing membrane comprises occlusive Scotchpak 9730® obtainable from 3M.

The release liner is typically disposed on an opposite surface of the pharmaceutical formulation layer to the backing membrane and provides a removable protective or impermeable layer, usually but not necessarily rendered non-stick so as to not adhere to the pharmaceutical formulation layer. The release liner serves to protect the pharmaceutical formulation layer during storage and transit, and is intended to be removed during use. The release liner may be formed from the same materials used for the backing membrane, but may be formed from metal foils, Mylar®, polyethylene terephthalate, siliconized polyester, fumed silica in silicone rubber, polytretrafluoroethylene, cellophane, siliconized paper, aluminized paper, polyvinyl chloride film, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene, and styrene-isoprene copolymers, polyethylene, and polypropylene.

Suitably, the release liner is an occlusive or semi-occlusive backing film being compatible with the pharmaceutically-acceptable adhesive present in the pharmaceutical formulation layer.

Suitably, the release liner may be selected from Scotchpak 9741®, Scotchpak 1022®, Scotchpak 9742®, Scotchpak 9744®, Scotchpak 9748® and Scotchpak 9755®, all of which are obtainable from 3M and comprise fluoropolymers coated onto polypropylene or polyester film. Other suitable release liners made by other manufacturers may also be used. The release liner may be of any thickness known in the art. Suitably the release liner has a thickness of about 0.01 mm to about 2 mm.

In one embodiment, the release liner is Scotchpak 9741®. In another embodiment, the release liner is Scotchpak 1022®.

The container or closure system may be made from a range of materials suitable for protecting the packaged transdermal patch from moisture and light.

Permeation Rate of Ropivacaine or Opioid

As previously stated, the present invention provides a transdermal patch comprising a pharmaceutical formulation, said formulation comprising ropivacaine or an opioid and a pharmaceutically-acceptable adhesive, and wherein said formulation has an in vitro human skin permeation rate of ropivacaine or opioid that is greater than 1.8 μg cm$^{-2}$ h$^{-1}$. The permeation of ropivacaine or opioid through human skin has been measured for selected patches and saturated solutions. Permeation/release measurements of ropivacaine or opioid through a 9% EVA membrane were used as a tool to select candidate patches. Permeation/release data was only recorded for those patches that remained free of ropivacaine or opioid precipitation (i.e. those that were below saturation concentration).

The present invention also provides a pharmaceutical formulation, said formulation comprising ropivacaine or opioid and a pharmaceutically-acceptable adhesive, and wherein said formulation has an in vitro human skin permeation rate of ropivacaine or opioid that is greater than 1.8 μg cm$^{-2}$ h$^{-1}$.

By in vitro human skin permeation rate we mean the rate of delivery of ropivacaine or opioid through human epidermal membranes at time periods up to 12 hours.

Suitably, the in vitro human skin permeation rate of ropivacaine or opioid is the apparent steady state flux (calculated from the approximately linear portion of the cumulative permeation profile), typically observed between 3 and 12 hours, or between 4 and 12 hours, when assessed under the conditions detailed in the following sections.

In an embodiment, the in vitro human skin permeation rate of ropivacaine or opioid is between 1.8 μg cm$^{-2}$ h$^{-1}$ and 10 μg cm$^{-2}$ h$^{-1}$.

In a further embodiment, the in vitro human skin permeation rate of ropivacaine or opioid is between 2 μg cm$^{-2}$ h$^{-1}$ and 6 μg cm$^{-2}$ h$^{-1}$.

In a further embodiment, the in vitro human skin permeation rate of ropivacaine or opioid is between 3 μg cm$^{-2}$ h$^{-1}$ and 5 μg cm$^{-2}$ h$^{-1}$.

Pharmaceutical-Acceptable Adhesive

The pharmaceutically-acceptable adhesive is selected both in terms of its ability to solubilise ropivacaine or an opioid, and its adhesive tack and peel properties.

In one embodiment, the adhesive has a ropivacaine or opioid solubility in excess of 2.5% w/w at room temperature.

Any suitable adhesive may be used. In an embodiment, the adhesive is selected from acrylate/polyacrylate materials, rubbers and silicones. Suitably, the adhesive is an acrylate or polyacrylate material, including acrylate copolymers and acrylate-vinyl acetate, such as Duro-Tak 87-2677®, Duro-Tak 87-900A®, Duro-Tak 87-2074®, Duro-Tak 87-2054®, Duro-Tak 87-2052®, Duro-Tak 87-2196®, obtainable from Henkel.

In another embodiment, the adhesive is selected from Duro-Tak 87-900A®, Duro-Tak 87-2677® and Duro-Tak 87-2074®, having approximately 4% (w/w), 8% (w/w) and 12% (w/w) ropivacaine solubility respectively and exhibiting excellent peel and tack performance.

Suitably, the adhesive is Duro-Tak 87-2677®.

In one embodiment, a suitable volatile solvent is added to the adhesive to reduce viscosity and aid solvation. Suitable solvents may include, but are not limited to, isopropyl alcohol, methanol, ethanol and ethyl acetate.

Typically, the amount of adhesive is between 58 and 97% w/w.

Carrier Oil

The carrier oil is selected both for its compatibility with the pharmaceutically-acceptable adhesive and for its ability to solubilise ropivacaine or the opioid. Carrier oils used in conjunction with the present invention include, but are not limited to, sorbitan monooleate, sorbitan trioleate, triglycerides of carprylic/capric acid, propylene glycol dicaprylate/dicaprate, ethoxy diglycol, propylene glycol monocaprylate, glycerol monooleate, lanolin, acetylated lanolin, polyethylene glycol lanolin, glycerol monocaprylate/caprate, propylene glycol laurate, and/or mono- or diglycerides of capric acid.

Suitably, the carrier oil has a water solubility of less than 0.1% (w/w) and a ropivacaine or opioid solubility in excess of 3% (w/w).

Suitably, the carrier oil may be sorbitan trioleate, propylene glycol monocaprylate, glycerol monocaprylate/caprate, propylene glycol laurate, and/or mono- or diglycerides of capric acid. Suitably, the carrier oil is present in the pharmaceutical formulation at a concentration of between about 2.5% (w/w) and about 35% (w/w).

In one embodiment, the carrier oil is in an amount of between 9 and 21% w/w.

Suitably, the carrier oil is in an amount of between 12 and 21% w/w.

Suitably, the carrier oil has a ropivacaine or opioid solubility in excess of 4% (w/w).

Suitably, the carrier oil may be propylene glycol monocaprylate, propylene glycol laurate and/or mono- or diglycerides of capric acid. Even more suitably, the carrier oil is propylene glycol monocaprylate, obtainable under the trade name Capryol 90®.

In one embodiment, the carrier oil is included in the pharmaceutical formulation without any other excipients.

Suitably, the carrier oil is included in the pharmaceutical formulation as part of a ternary mixture including both a penetration enhancer and a hydrophilic material.

In another embodiment, the carrier oil is included in the pharmaceutical formulation as part of a quaternary mixture including a penetration enhancer, a hydrophilic material, and an additive selected from non-ionic surfactants, hydrophilic surfactants, terpenes and dual membrane disruptors, including those obtainable under the trade names Transcutol®, Brij® 98®, Tween 80®, Cremphor EL® and menthol.

Penetration Enhancer

The penetration enhancers used in conjunction with the present invention serve to promote the percutaneous absorption of ropivacaine or opioid by temporarily diminishing the impermeability of the skin. Importantly, when included in the pharmaceutical formulations of the present invention, the penetration enhancer must not compromise the release characteristics of the adhesive.

Suitably, the penetration enhancer and the quantities in which it is added should be non-toxic, non-irritating, non-allergenic, odourless, tasteless, colourless, soluble, and compatible with ropivacaine or the opioid and the other excipients herein described. Importantly, the enhancer should not lead to the loss of bodily fluids, electrolytes and other endogenous materials, and skin should immediately regain its barrier properties on its removal. Examples of penetration enhancers suitable for inclusion into the pharmaceutical formulation of the present invention include, but are not limited to, sugar fatty acid esters and ethers, $C_8$-$C_{18}$ fatty alcohol, azone, oleic ethers, terpenes and ethoxy ethanols. Suitably, when used, the penetration enhancer is present in the pharmaceutical formulation at a concentration of between about 1.4% (w/w) and about 15% (w/w).

Suitably, the penetration enhancer is in an amount of between 1.5 and 4% w/w.

Suitably, the penetration enhancer may be polyoxyethylene oleyl ether, obtainable under the trade name Brij 93®, or 2-(2-ethoxyethoxy)ethanol, obtainable under the trade name Transcutol®, or menthol.

In one embodiment, the penetration enhancer is included in the pharmaceutical formulation without any other excipients.

In another embodiment, the penetration enhancer is included in the pharmaceutical formulation as part of a binary mixture including either a carrier oil or a hydrophilic material.

Suitably, the penetration enhancer is included in the pharmaceutical formulation as part of a ternary mixture including both a carrier oil and a hydrophilic material.

In another embodiment, the penetration enhancer is included in the pharmaceutical formulation as part of a quaternary mixture including a carrier oil, a hydrophilic material, and an additive selected from non-ionic surfactants, hydrophilic surfactants, terpenes (such as menthol) and membrane disruptors, including those obtainable under the trade names Transcutol®, Brij 98®, Tween 80®, and Cremphor EL®.

Hydrophilic Material

The hydrophilic materials used in conjunction with the present invention may aid the skin absorption of the ropivacaine or opioid. The hydrophilic material may be present as a polar enhancer, and is liquid at skin temperature. Suitably, the hydrophilic material and the quantities in which it is added should be non-toxic, non-irritating, non-allergenic, odourless, tasteless, colourless, soluble, and compatible with the ropivacaine or opioid and the other excipients herein described.

In one embodiment, the hydrophilic material will have a hydrophilic-lipophilic balance (HLB) of greater than 7. Examples of hydrophilic materials suitable for inclusion into the pharmaceutical formulation of the present invention include, but are not limited to, propylene glycol, glycerol, polyethylene glycol, short chain water soluble esters of citric acid, acetic acid, hexylene glycol and alcohols, including diols and polyols. Suitably, when used, the hydrophilic material is present in the pharmaceutical formulation at a concentration of between about 1.5% (w/w) and about 20% (w/w).

Suitably, the hydrophilic material is in an amount of between 6 and 11% w/w.

Suitably, the hydrophilic material is propylene glycol.

In an embodiment, the hydrophilic material is included in the pharmaceutical formulation as part of a binary mixture including either a carrier oil or a penetration enhancer.

Suitably, the hydrophilic material is included in the pharmaceutical formulation as part of a ternary mixture including both a carrier oil and a penetration enhancer.

In another embodiment, the hydrophilic material is included in the pharmaceutical formulation as part of a quaternary mixture including a carrier oil, a penetration enhancer, and an additive selected from non-ionic surfactants, hydrophilic surfactants, terpenes (such as menthol) and membrane disruptors, including those materials obtainable under the trade names Transcutol®, Brij 98®, Tween 80®, and Cremphor EL®.

Excipient Combinations

As indicated in the foregoing paragraphs, the pharmaceutical formulations of the present invention optionally comprise one or more excipients in addition to the ropivacaine or opioid and the pharmaceutically-acceptable adhesive.

Suitably, the pharmaceutical formulation comprises two excipients present as a binary mixture and, more suitably, the pharmaceutical formulation comprises three excipients present as a ternary mixture.

It has been demonstrated that for pharmaceutical formulations containing ternary mixtures of excipients, improved transdermal delivery of ropivacaine or an opioid may be achieved.

The binary or ternary mixtures may improve the transdermal delivery of the ropivacaine or opioid by temporary alteration of the skin barrier function, or by improvements in drug/skin partitioning resulting from increased solubility of the drug in the stratum corneum. The selection of binary/ternary/quaternary mixtures is designed to maintain reasonable solubility of the ropivacaine or opioid in the pharmaceutically-acceptable adhesive. It is not necessary for the binary/ternary/quaternary mixture to increase drug solubility in the pharmaceutically-acceptable adhesive. In certain embodiments the solubility of the ropivacaine or opioid in the selected ternary mixtures of excipients is greater than the solubility of the ropivacaine or opioid in each individual excipient. In such embodiments, the observed solubility is significantly greater than the predicted solubility based upon proportional contributions from the solubilities in individual excipients, suggesting a significant cooperative effect on drug solubility.

The inclusion of one or both of a penetration enhancer and/or a hydrophilic material in the binary or ternary mixtures may contribute to improving transdermal ropivacaine or opioid delivery by increasing skin permeation according to the mechanisms discussed in the preceding paragraphs.

Binary Mixtures

The binary mixtures for use in conjunction with the present invention contain two excipients selected from a carrier oil, a penetration enhancer and/or a hydrophilic material.

In one embodiment, the quantity of binary mixture present in the pharmaceutical formulations is from about 5% (w/w) to about 40% (w/w). Suitably, from about 10% (w/w) to about 35% (w/w).

Optionally, the binary mixture may contain one or more additives, selected from the group consisting of non-ionic surfactants, hydrophilic surfactants, terpenes (such as menthol) and membrane disruptors. Suitable additives include, but are not limited to those obtainable under the trade names Transcutol®, Brij 98®, Tween 80®, and Cremphor EL®.

In one embodiment, the binary mixture comprises a penetration enhancer selected from the group consisting of polyoxyethylene oleyl ether, obtainable under the trade name Brij 93®, or 2-(2-ethoxyethoxy)ethanol, obtainable under the trade name Transcutol®, and a hydrophilic material selected from the group consisting of propylene glycol, glycerol, polyethylene glycol, short chain water soluble esters of citric acid, acetic acid, hexylene glycol and alcohols, including diols and polyols.

In another embodiment, the binary mixture comprises a carrier oil selected from the group consisting of propylene glycol monocaprylate, propylene glycol laurate and/or mono- or diglycerides of capric acid, and a penetration enhancer selected from the group consisting of polyoxyethylene oleyl ether, obtainable under the trade name Brij 93®, or 2-(2-ethoxyethoxy)ethanol, obtainable under the trade name Transcutol®.

Suitably, the binary mixture comprises propylene glycol monocaprylate, obtainable under the trade name Capryol 90®, and polyoxyethylene oleyl ether, obtainable under the trade name Brij 93®.

In another embodiment, the binary mixture comprises a carrier oil selected from the group consisting of propylene glycol monocaprylate, propylene glycol laurate and/or mono- or diglycerides of capric acid, and a hydrophilic material selected from the group consisting of propylene glycol, glycerol, polyethylene glycol, short chain water soluble esters of citric acid, acetic acid, hexylene glycol and alcohols, including diols and polyols.

Suitably, the binary mixture comprises propylene glycol monocaprylate, obtainable under the trade name Capryol 90®, and propylene glycol.

Ternary Mixtures

The ternary mixtures for use in conjunction with the present invention contain a carrier oil, a penetration enhancer and a hydrophilic material.

In one embodiment, the quantity of ternary mixture present in the pharmaceutical formulations is from about 10% (w/w) to about 40% (w/w), suitably from about 15% (w/w) to about 35% (w/w), and more suitably about 35% (w/w).

Optionally, the ternary mixture may contain one or more additives, selected from the group consisting of non-ionic surfactants, hydrophilic surfactants, terpenes (such as menthol) and membrane disruptors. Suitable additives include, but are not limited to those obtainable under the trade names Transcutol®, Brij 98®, Tween 80®, and Cremphor EL®.

In one embodiment, the ternary mixture comprises a carrier oil selected from the group consisting of propylene glycol monocaprylate, propylene glycol laurate and/or mono- or diglycerides of capric acid; a penetration enhancer selected from the group consisting of polyoxyethylene oleyl ether, obtainable under the trade name Brij 93®, or 2-(2-ethoxyethoxy)ethanol, obtainable under the trade name Transcutol®; and a hydrophilic material selected from the group consisting of propylene glycol, glycerol, polyethylene glycol, short chain water soluble esters of citric acid, acetic acid, hexylene glycol and alcohols, including diols and polyols.

Suitably, the ternary mixture comprises propylene glycol monocaprylate, obtainable under the trade name Capryol 90®; polyoxyethylene oleyl ether, obtainable under the trade name Brij 93®; and propylene glycol.

Preparation of Pharmaceutical Formulations

The pharmaceutical formulations of the present invention can be prepared using conventional techniques known in the art.

The pharmaceutical formulations are suitably prepared by mixing all of the components together.

The individual components may be mixed by simply adding all of the components at the same time into a mixing vessel and then mixing them all together (a "one-pot" mixture). Alternatively, the components may be added sequentially in two or more steps or stages. Suitably, where more than one excipient forms part of the formulation, such excipients may be pre-mixed to form binary or ternary excipient mixtures, which may themselves be subsequently mixed with the other components of the formulation.

Other experimental conditions required to prepare the formulations of the present invention, such as mixing times, mixing equipment, temperature control etc. can be readily determined by a person of ordinary skill in the art.

Further experimental details will also be evident from the accompanying Examples.

Once prepared, the pharmaceutical formulations of the present invention are formed into a transdermal patch for topical application.

Therapeutic Uses

The pharmaceutical formulations of the present invention are particularly suited to the treatment of pain. Once administered, the transdermal patch comprising the pharmaceutical formulation provides a localised delivery of the ropivacaine or opioid, thus providing pain relief at a desired location. During localised delivery, quantities of the ropivacaine or opioid may be absorbed into the patient's blood stream, thereby providing an additional, systemic delivery of the anaesthetic.

Types of pain that can be treated with the transdermal patch of the present invention include nociceptive and neuropathic pain.

Nociceptive pain may be pain associated with tissue irritation, impending injury, or actual injury, and is often characterized as aching and/or direct pains. Examples of conditions associated with nociceptive pain include bone fractures, burns, bumps, bruises, inflammation (from an infection or arthritic disorder), arthralgia, general myalgia and more specific myalgia caused by symptoms categorized generally as amplified musculoskeletal pain (AMP) syndrome.

Neuropathic pain is pain caused by damage or disease that affects the somatosensory system. The pain is typically characterized by burning, lancinating, coldness or so-called pins-and-needles-type sensations. Persistent allodynia— pain resulting from a non-painful stimulus such as a light touch—is also a common characteristic of neuropathic pain. The pain itself may have continuous and/or episodic (paroxysmal) components, the having electric shock-like qualities. Common causes of painful peripheral neuropathies that can be treated with the transdermal patches of the present invention include herpes zoster, infection, HIV-related neuropathies, nutritional deficiencies, toxins, remote manifestations of malignancies, immune mediated disorders and physical trauma to a nerve trunk. Neuropathic pain is also common in cases of cancer, either as a direct result of a cancer on peripheral nerves (for example through compression by a tumour), or as a side effect of chemotherapy radiation, injury or surgery.

The transdermal patches of the present invention may also prove effective in cases where the pain is be caused by a complex mixture of nociceptive and neuropathic factors, for example, myofascial pain.

The pharmaceutical compositions of the present invention may be used on their own as the sole therapy. Alternatively, the compositions may be administered as part of a combination therapy with one or more other pain treatments or anaesthetics. Such conjoint treatment may be achieved by way of the simultaneous, sequential or separate administration of the individual components of the treatment.

DETAILED DESCRIPTION OF THE DRAWINGS

The present invention is further defined with reference to the accompanying figures, in which data are presented as mean±standard error (SE), and where:

FIG. 1 compares the permeation, over 48 hours, of ropivacaine from a variety of transdermal patches of the present invention, with a ropivacaine saturated aqueous solution and a ropivacaine saturated citrate acetate buffer solution at pH 5, using continuous EVA (3M 9702) membrane.

Figure 2:
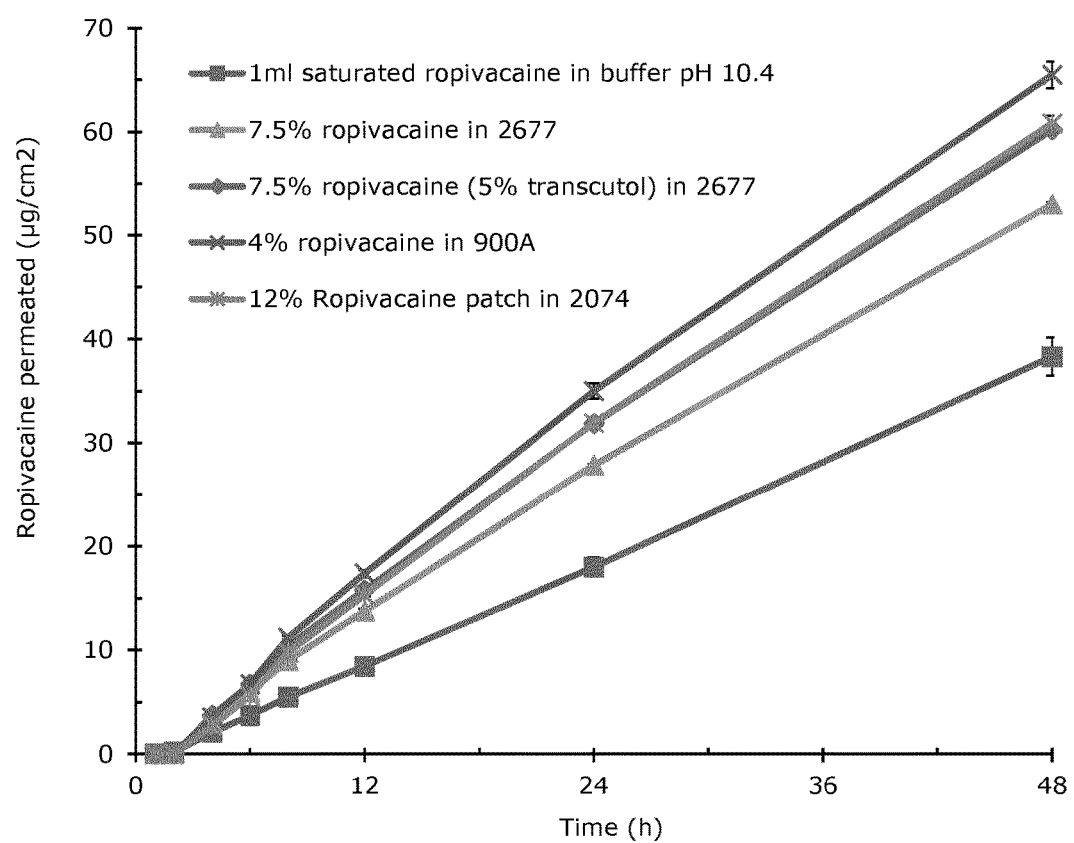

FIG. 2 compares the permeation, over 48 hours, of ropivacaine from a variety of transdermal patches of the present invention, with a ropivacaine saturated aqueous solution using continuous EVA (3M 9702) membrane.

Figure 3:
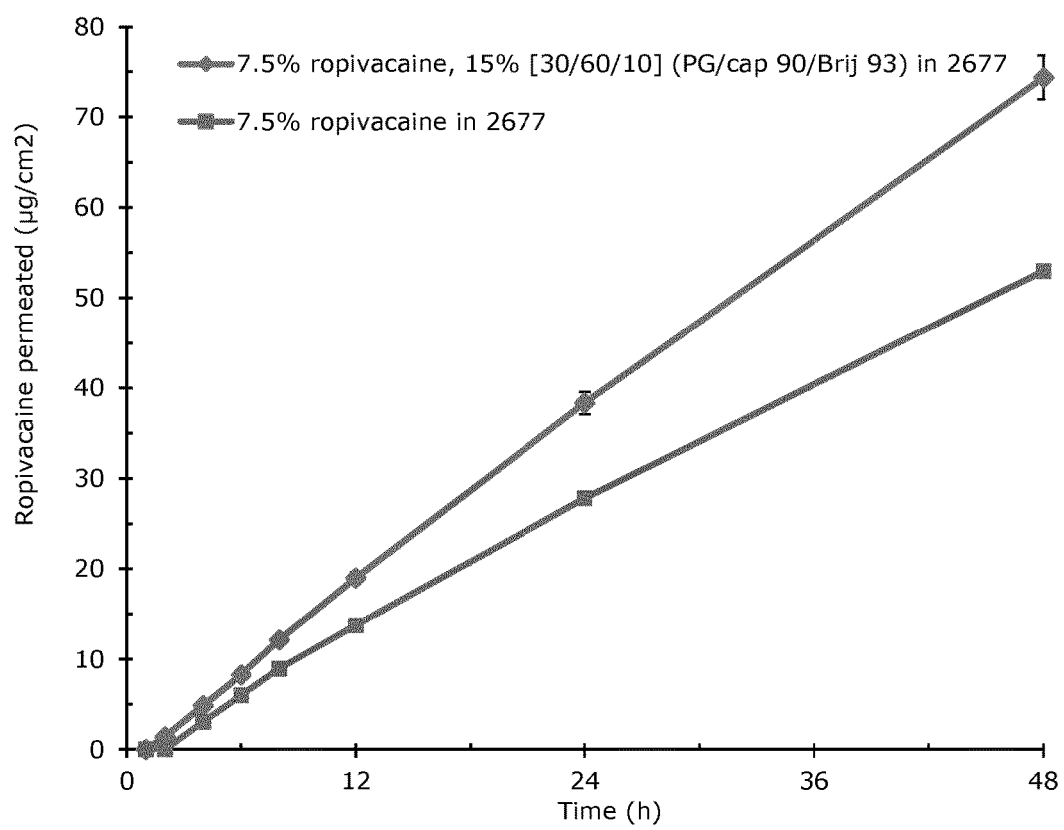

FIG. 3 compares the permeation, over 48 hours, of ropivacaine from a simple ropivacaine-in-adhesive (Duro-Tak® 87-2677) patch, with one containing 15% (w/w) of a ternary propylene glycol, Capryol® 90, Brij® 93 (30/60/10) excipient mixture, using continuous EVA (3M 9702) membrane.

Figure 4:
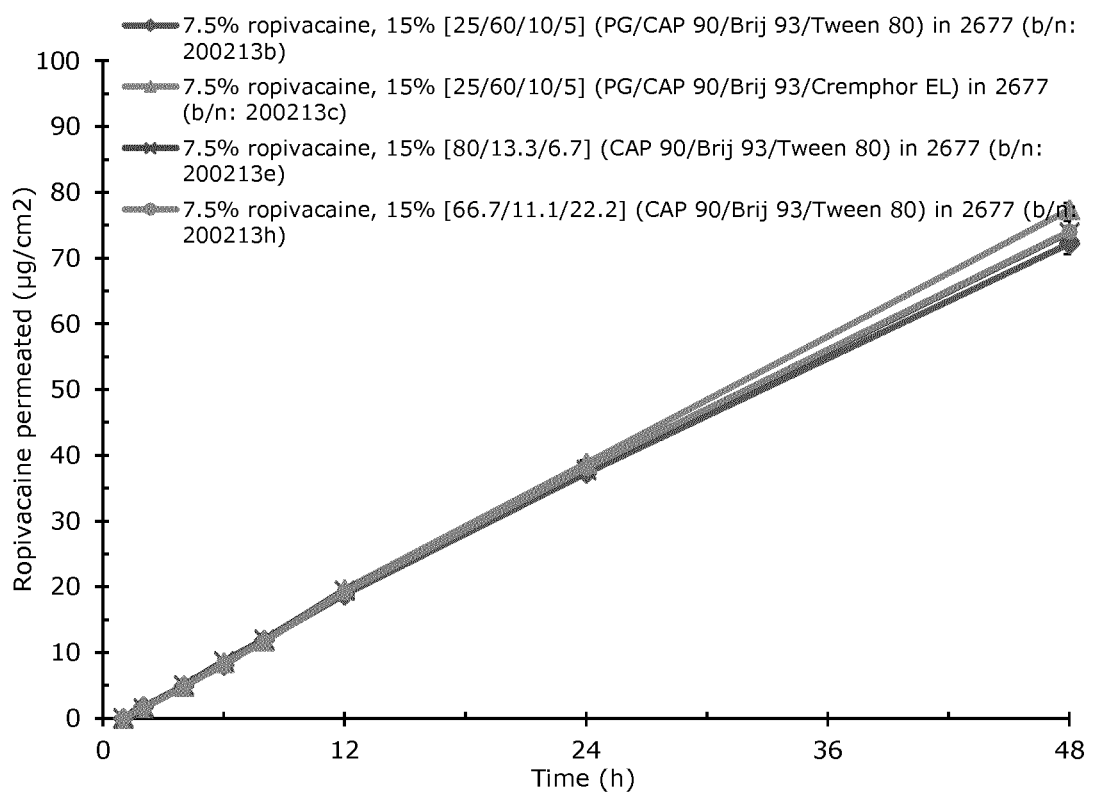

FIG. 4 compares the permeation, over 48 hours, of ropivacaine from various transdermal patches of the present invention, using continuous EVA (3M 9702) membrane.

Figure 5:
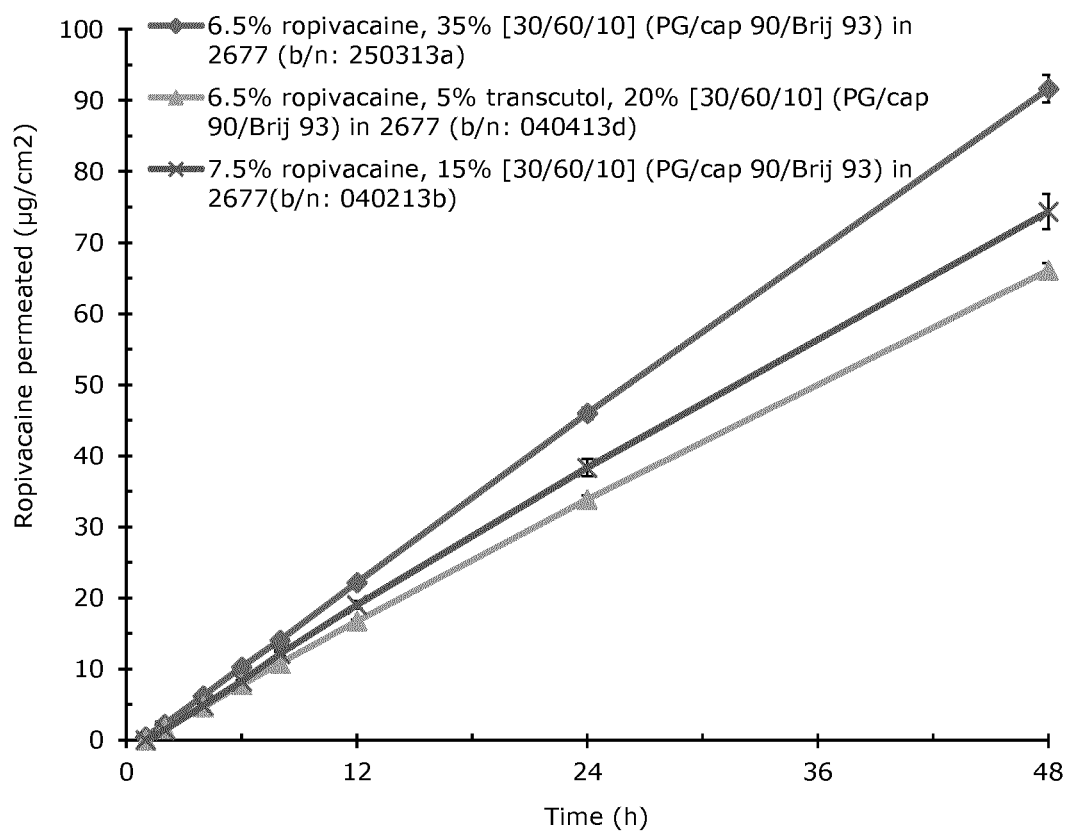

FIG. 5 compares the permeation, over 48 hours, of ropivacaine from various transdermal patches of the present invention, using continuous EVA (3M 9702) membrane.

Figure 6:
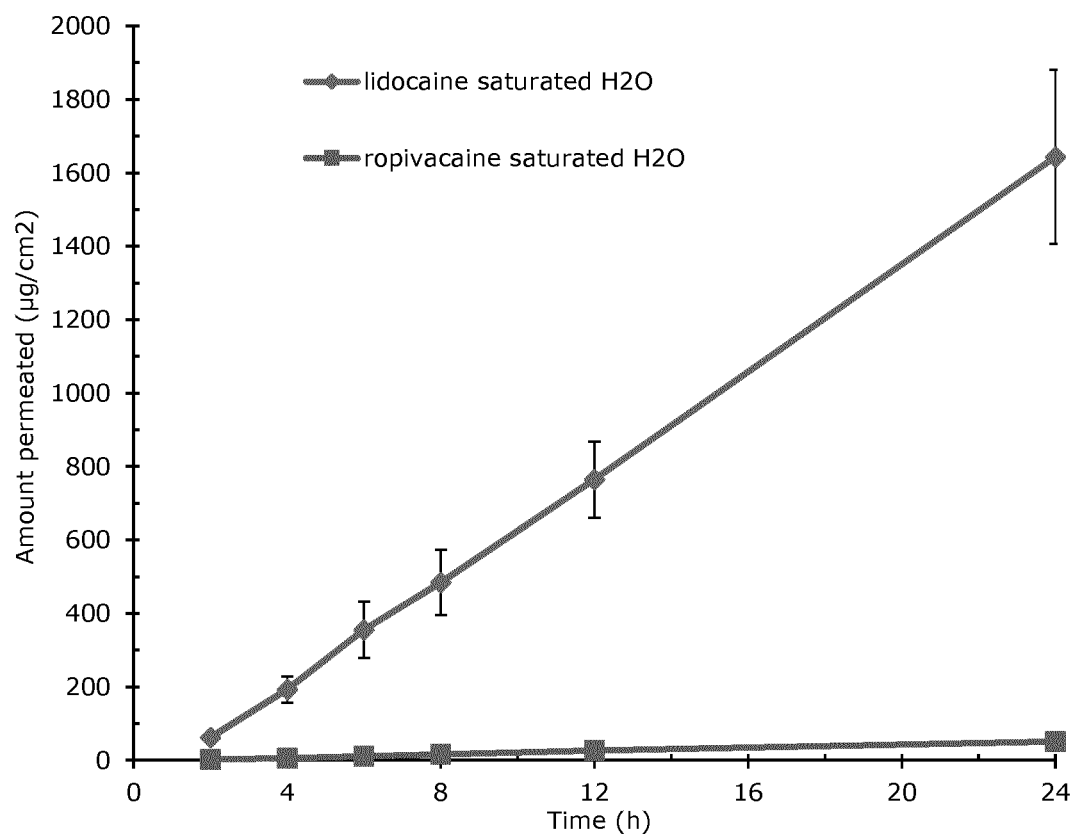

FIG. 6 compares the in vitro human skin permeation properties of a saturated ropivacaine solution versus those of a saturated lignocaine solution.

Figure 7:
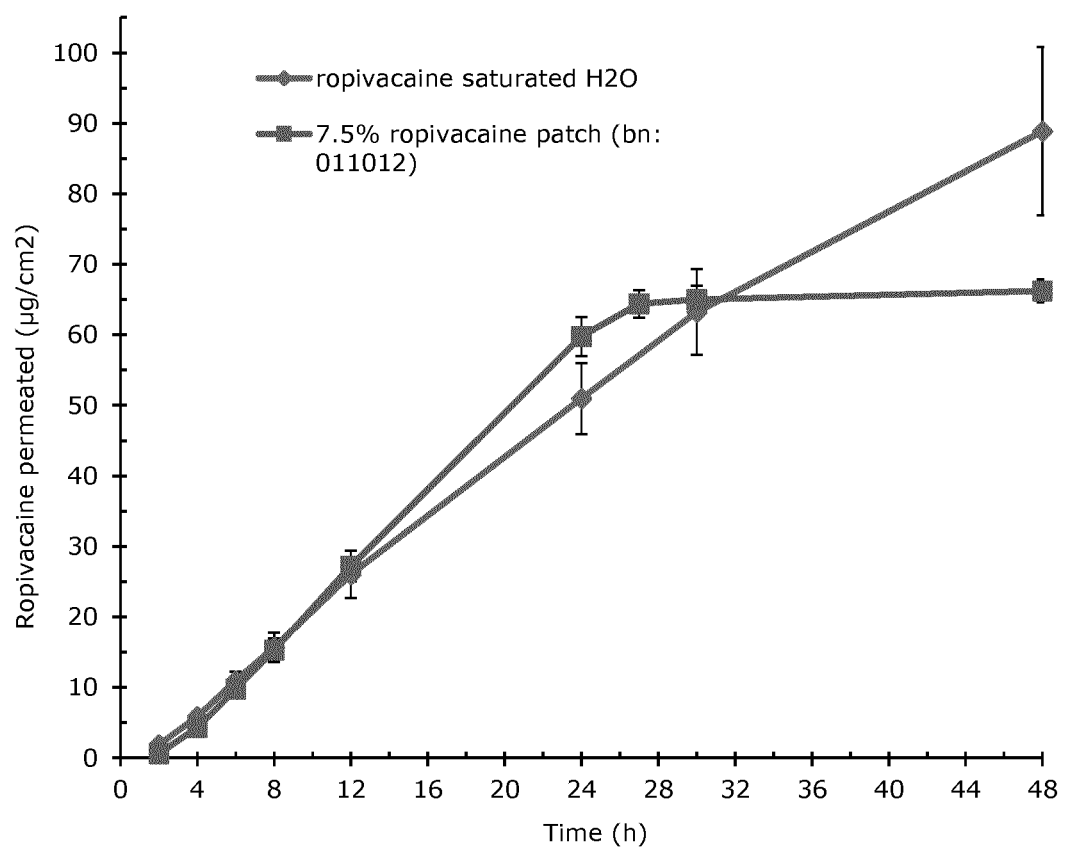

FIG. 7 compares the in vitro human skin permeation, over 48 hours, of ropivacaine from a patch containing 7.5% (w/w) ropivacaine in Duro-Tak® 87-2677 adhesive, with a simple ropivacaine-saturated solution.

Figure 8:
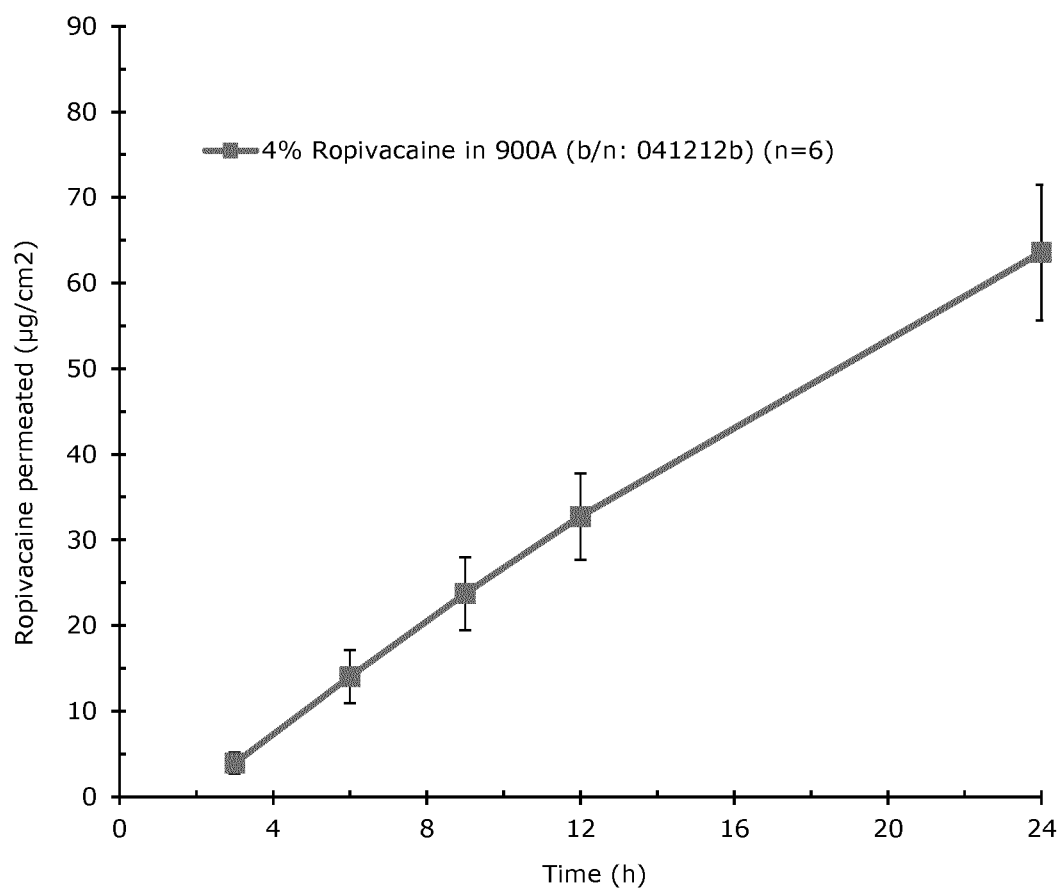

FIG. 8 demonstrates the in vitro human skin permeation, over 48 hours, of ropivacaine from a patch containing 4% (w/w) ropivacaine in Duro-Tak® 87-900A adhesive.

Figure 9:
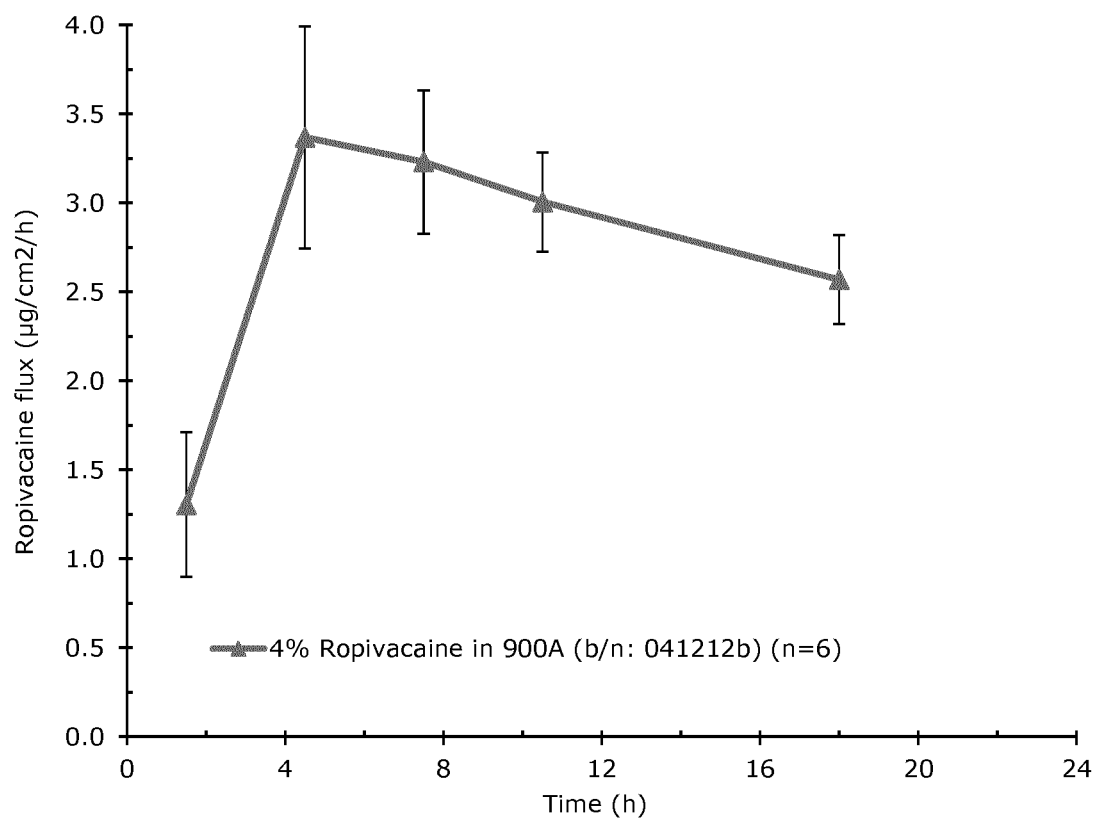

FIG. 9 demonstrates the mid time-point flux ($\mu g/cm^2\ h^{-1}$) of ropivacaine for a 4% (w/w) ropivacaine in Duro-Tak® 87-900A transdermal patch.

Figure 10:
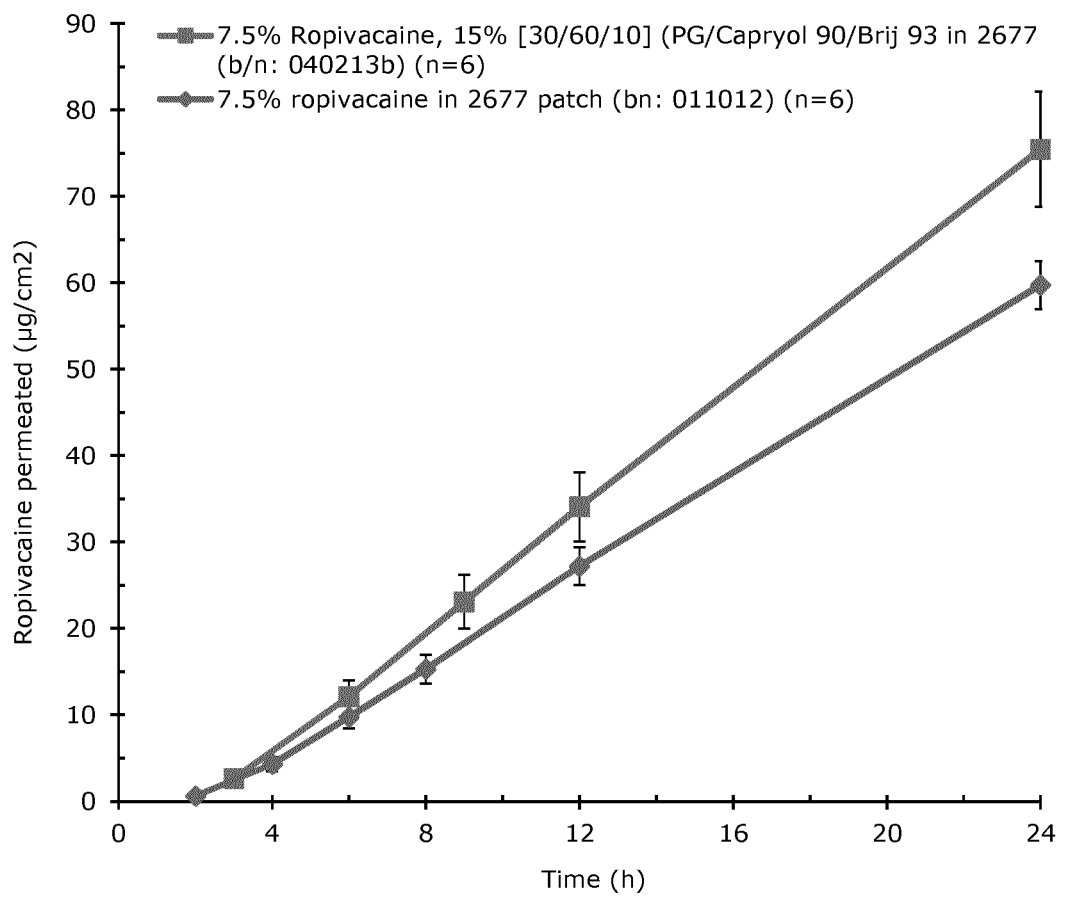

FIG. 10 compares the in vitro human skin permeation, over 24 hours, of ropivacaine from a patch containing 7.5% (w/w) ropivacaine in Duro-Tak® 87-2677 adhesive, with an identical patch containing 15% (w/w) of a ternary propylene glycol, Capryol® 90, Brij® 93 (30/60/10) excipient mixture.

Figure 11:
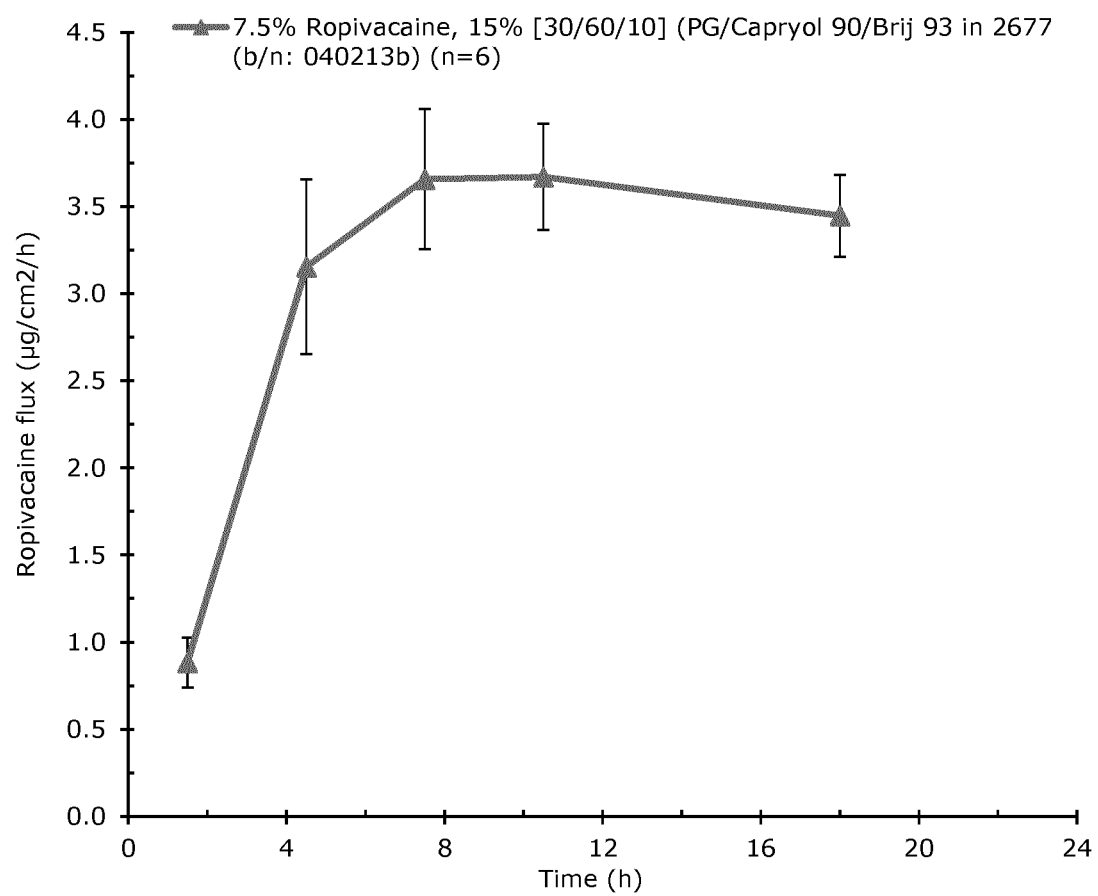

FIG. 11 demonstrates the mid time-point flux ($\mu g/cm^2\ h^{-1}$) of ropivacaine for a transdermal patch containing 7.5% (w/w) ropivacaine and 15% (w/w) of a ternary propylene glycol, Capryol® 90, Brij® 93 (30/60/10) excipient mixture in Duro-Tak® 87-2677 adhesive.

Figure 12:
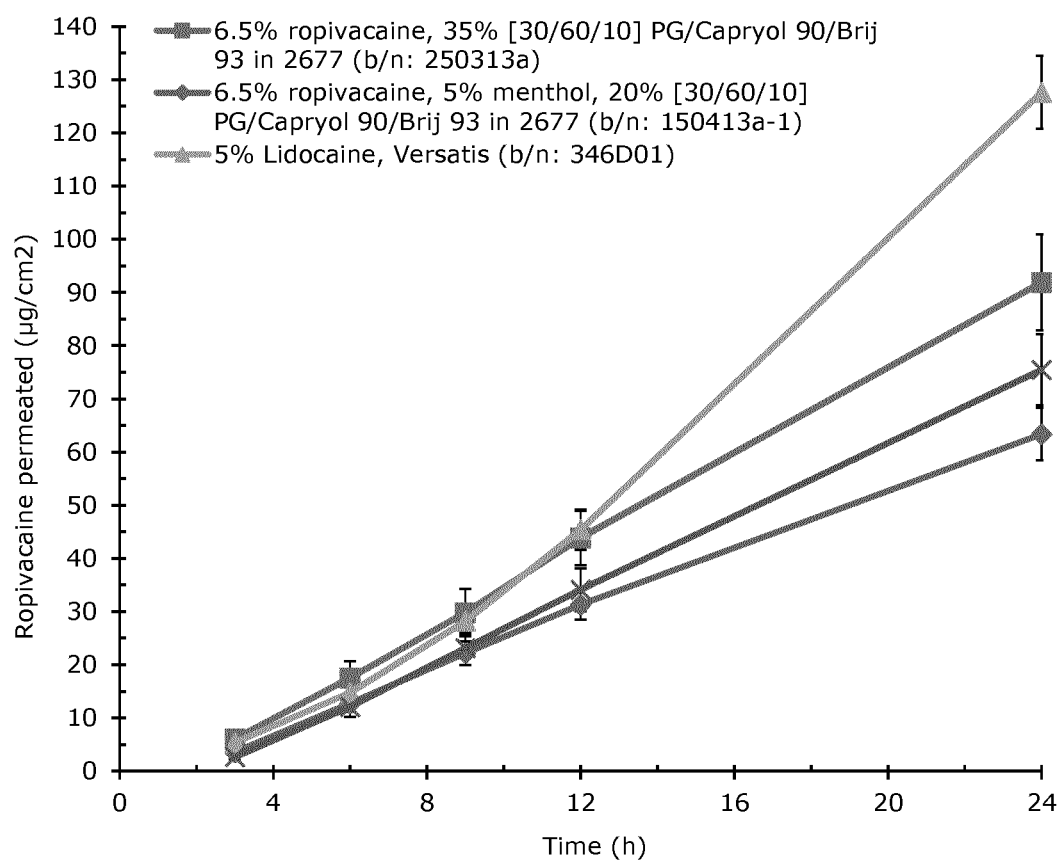

FIG. 12 compares the in vitro human skin permeation, over 24 hours, of ropivacaine from various transdermal patches of the present invention, with a commercially-available lidocaine transdermal patch (Verstatis).

Figure 13:
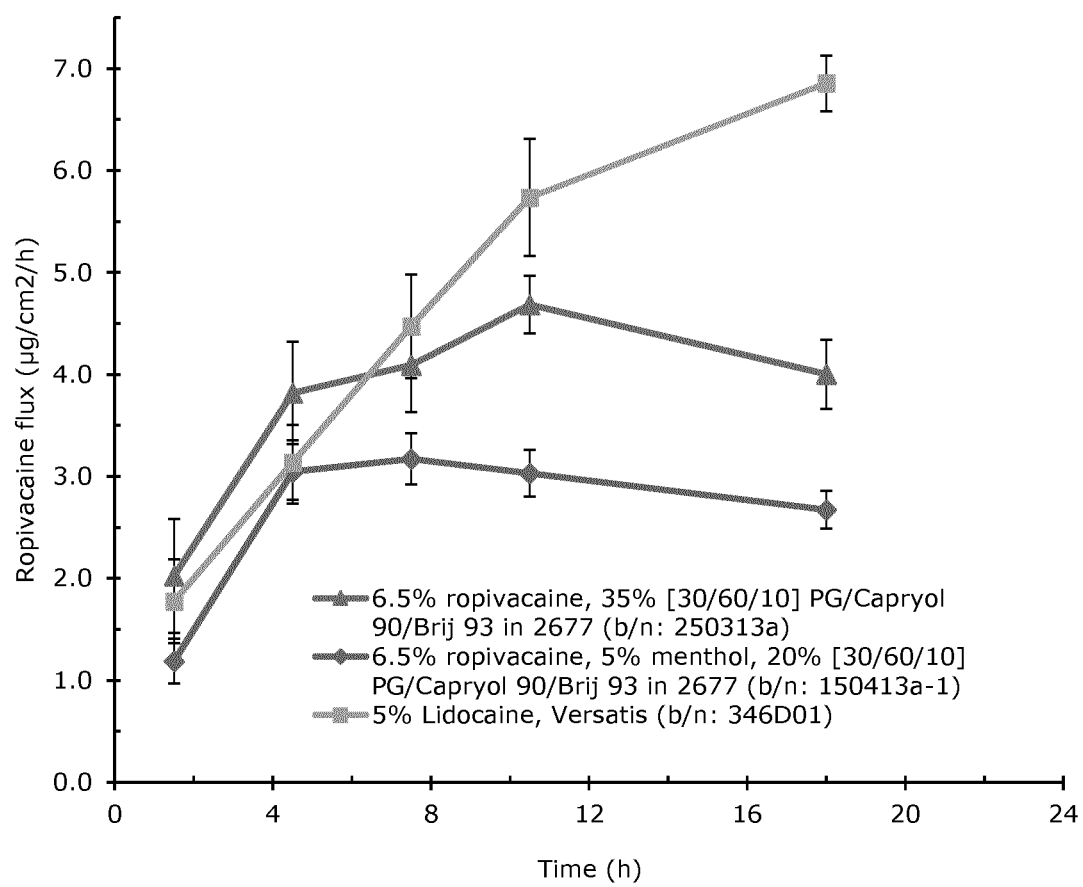

FIG. 13 compares the mid time-point flux ($\mu g/cm^2\ h^{-1}$) of ropivacaine for various transdermal patches of the present invention, with that of lidocaine from a commercially-available lidocaine transdermal patch (Verstatis).

EXAMPLES

Solubility Assessment

Adhesive Only Patches

Initial solubility was assessed visually in the wet adhesive prior to casting. Only mixtures where the drug had fully dissolved were cast. Mixtures were cast onto a suitable release liner and dried prior to laminating with an occlusive backing membrane, with a small portion being laminated with release liner. This provided a section of patch that could easily be prepared for microscopic evaluation (via transfer to a glass slide). Solubility in the dried adhesive mixture was assessed visually and by polarised microscopy. The presence of precipitate indicated that the drug loading was above saturation.

Duro-Takx adhesives 87-2677, 87-900A and 87-2074 were chosen as lead adhesives based on their solubility for ropivacaine. The solubilities were ≥7.5<10% (w/w), ≥4<5% (w/w) and ≥12<14% (w/w) respectively, as indicated in Table 1 below:

TABLE 1

Selected pharmaceutically-acceptable adhesives and their solubility (% w/w) for ropivacaine

| Adhesive | Functional groups | Chemical composition | % solids | Apparent ropivacaine solubility (%) |
|---|---|---|---|---|
| DURO-TAK 87-900A | None | acrylate copolymer | 43.88 | ≥4 < 5% |

TABLE 1-continued

Selected pharmaceutically-acceptable adhesives and their solubility (% w/w) for ropivacaine

| Adhesive | Functional groups | Chemical composition | % solids | Apparent ropivacaine solubility (%) |
|---|---|---|---|---|
| DURO-TAK 87-2677 | —COOH | acrylate-vinylacetate | 38.68 | ≥7.5 < 10% |
| DURO-TAK 87-2074 | —COOH/—OH | acrylate | 28.38 | ≥12 < 14% |

Solubility Enhancement with Excipients

Combinations of adhesive and individual, or mixtures of, excipients were studied with a view to improve the solubility of ropivacaine, and therefore possibly increase its delivery rate from the transdermal patch. Moreover, the inclusion of one or more excipients in the pharmaceutical formulation, including penetration enhancers and hydrophilic materials, was advantageous for the purpose of enhancing skin penetration.

A series of excipients were selected for ropivacaine solubility investigation, as seen in Table 2 below. Approximate solubilities were assessed visually by gradual addition of ropivacaine to a known volume of excipient at room temperature until saturation was observed.

TABLE 2

Ropivacaine solubility (% w/v) in candidate excipients

| Excipient | Chemical name | HLB | % Solubility |
|---|---|---|---|
| IPM | isopropylmyristate | 11.5 | 0.7-1.4 |
| Labrafil M 1944 CS | apricot kernel oil PEG-6 esters | 4 | 1.2-2.1 |
| DMI | dimethylisosorbide | — | 2.8-3.6 |
| Tween 80 | polyethylene glycol sorbitan monooleate | 15 | <0.12 |
| Crodamol EO | ethyl oleate | 11 | 0.5-1.2 |
| PEG 200 | Poly(ethylene glycol) | — | <1 |
| PEG 300 | Poly(ethylene glycol) | — | <1 |

HLB—Hydrophilic-lipophilic balance

Further excipients were assessed for ropivacaine solubility and compatibility with Duro-Tak® adhesive 87-900A. Adhesive compatibility was assessed by mixing ropivacaine (4% (w/w)) and excipient (5% (w/w)) with Duro-Tak® 87-900A. Mixtures that were miscible were cast at a wet thickness of 350 μm onto 3M 9741 release liner, and then dried and laminated with 3M 9730 occlusive backing membrane. Successful castings demonstrated no precipitate after 72 hours. Adhesive-compatible excipients were then subjected to solubility testing according to the protocol described above, see Table 3 below:

TABLE 3

Ropivacaine solubility (% w/v) in candidate excipients, showing compatibility with Duro-Tak ® 87-900A

| Excipient | Chemical name | HLB | 900A Compatible | % Solubility |
|---|---|---|---|---|
| Span 80 | sorbitan monooleate | 4.3 | no | — |
| Span 85 | sorbitan trioleate | 1.8 | yes | 3.1-3.9 |
| Captex 355 | triglycerides of caprylic/capric acid | — | yes | 0.2-1.2 |
| Labrafac PG | propylene glycol dicaprylate/dicaprate | 2 | yes | 1.3-1.8 |
| Transcutol P | ethoxy diglycol | 4.2 | yes | 4.1-4.6 |
| Capryol 90 | propylene glycol monocaprylate | 6 | yes | 6.3-7.4 |
| Capmul-GMO-50 | glycerol monooleate | 3-4 | no | — |
| Medilan-SO-(RB) | lanolin | 4 | no | — |
| Modulan | acetylated lanolin | — | no | — |
| Solulan-75 | PEG-75 lanolin | — | no | — |
| Capmul-MCM-EP | glycerol monocaprylate/caprate | 5-6 | not assessed* | 4.5-5.1 |
| Lauroglycol 90 | propylene glycol laurate | 5 | not assessed* | 3.7-4.7 |
| Capmul-MCM-C8-EP | mono/diglycerides capric acid | 5-6 | not assessed* | 5.5-6.0 |

*compatibility with Duro-Tak ® 87-900A not assessed at this stage due to higher observed solubility in Capryol 90
HLB—Hydrophilic-lipophilic balance The ropivacaine solubilities of binary and ternary mixtures of excipients were studied in order to improve ropivacaine delivery. Furthermore, it was desirous to incorporate the skin permeation properties of more than one excipient.

Binary mixtures of Capryol 90® and Transcutol®—25/75, 50/50, 75/25 (% v/v)—were prepared and exhibited ropivacaine solubilities of ≥3.6<4.8% (w/v), ≥4.6<5.6% (w/v) and ≥4.6<5.2% (w/v) respectively.

Other binary and ternary mixtures of propylene glycol, Capryol 90® and Brij 93® seen in Table 4 were prepared on a w/w basis and stirred with an excess of ropivacaine in 20 ml vials for approximately 24 hours at room temperature. Aliquots of each mixture were then centrifuged, filtered, diluted (1/5000) with 50/50 acetonitrile and water, and analysed by HPLC. The ropivacaine solubilities of the binary and ternary mixtures are shown in Table 4 below:

TABLE 4

Ropivacaine solubility (% w/v) in binary and ternary excipient mixtures prepared on a w/w or w/w/w basis

| Mixture | % PG | % capryol 90 | % Brij 93 | % solubility |
|---|---|---|---|---|
| 1 | 100.0 | | | 1.93 |
| 2 | | 100.0 | | 5.87 |
| 3 | | | 100.0 | 1.83 |
| 4 | 34.0 | 33.1 | 32.8 | 4.81 |
| 5 | 79.9 | | 20.1 | 2.97 |
| 6 | | 79.9 | 20.1 | 5.42 |
| 7 | 50.0 | 50.0 | | 5.65 |
| 8 | 59.8 | 19.8 | 20.3 | 4.42 |
| 9 | 20.1 | 59.8 | 20.0 | 5.93 |
| 10 | 40.4 | 39.7 | 19.8 | 5.36 |
| 11 | 59.9 | 30.0 | 10.0 | 4.85 |
| 12 | 30.5 | 59.6 | 9.9 | 6.25 |
| 13 | 10.0 | 50.0 | 40.0 | 4.54 |
| 14 | 10.0 | 60.0 | 30.0 | 5.27 |
| 15 | 15.1 | 49.7 | 35.2 | 5.20 |

Further solubility assessment was performed on a variety of ternary and quaternary (ternary mixture plus additive) excipient mixtures, see Table 5. The excipients selected for analyses were propylene glycol, Capryol 90®, Brij 93®, Brij 98®, Tween 80® and Cremphor EL®. The excipient mixtures were prepared, and their ropivacaine solubilities were recorded, according to the protocols discussed above for binary and ternary excipient mixtures.

TABLE 5

Ropivacaine solubility (% w/v) in ternary and quaternary excipient mixtures prepared on a weight basis

| Mixture | % PG | % capryol 90 | % Brij 93 | % Brij 98 | % Tween 80 | % Cremphor EL | % solubility |
|---|---|---|---|---|---|---|---|
| 1 | 25.1 | 59.8 | 10.1 | 5.0 | | | 4.53 |
| 2 | 24.9 | 59.8 | 10.2 | | 5.1 | | 4.70 |
| 3 | 25.0 | 59.8 | 10.2 | | | 5.0 | 4.75 |
| 4 | | 79.9 | 13.3 | 6.8 | | | 4.21 |
| 5 | | 79.8 | 13.5 | | 6.6 | | 4.24 |
| 6 | | 80.0 | 13.3 | | | 6.7 | 4.28 |
| 7 | | 66.7 | 11.0 | 22.3 | | | 3.38 |
| 8 | | 66.8 | 11.0 | | 22.2 | | 3.60 |
| 9 | | 66.7 | 11.0 | | | 22.3 | 3.77 |

The solubility data presented in Tables 4 and 5 demonstrates flexibility in the binary, ternary and quaternary mixtures to be included in adhesives.

Preparation of Transdermal Patches

Adhesive Only Patches

Patch formulations were typically prepared with 4 g of (wet) adhesive.

Ropivacaine was weighed into a single vessel. Adhesive was then added and vessel was capped. The vessel contents were mixed using a roller mixer until the mixture became homogeneous and ropivacaine was fully dissolved. The adhesive mixture was then cast using a knife coater (Elcometer) at a suitable wet thickness onto a suitable release liner. Except for those patches incorporating menthol, a wet film thickness was selected to produce a dry film thickness of 70-95 µm, or suitably 80-85 µm. Typical casting thicknesses were 450 µm for Duro-Tak® 87-2677, 350 µm for Duro-Tak® 87-900A and 520 µm for Duro-Tak® 87-2074 adhesive mixtures resulting in dry film thicknesses ranging between 70-95 µm. The wet film was dried at room temperature for 15 minutes, then at 50° C. for 5 minutes, and finally at 90° C. for 10 minutes. The films were laminated with 3M 9730 occlusive polyester film laminate. Patches incorporating menthol were cast at lower wet thickness, typically 240-400 µm, and suitably 240 µm. These films were dried for 1 hour at room temperature, then for either 5 or 10 minutes at 50° C. Suitably the patches were dried at 50° C. for 5 minutes. Dry films ranged from 45 to 78 µm, suitably about 45 µm. Thinner films subjected to shorter drying times at 50° C. greatly reduced the loss of the volatile menthol component. The films incorporating menthol were laminated with 3M 9730 occlusive polyester film laminate.

Film thicknesses were measured using a digital micrometer. Patch thickness was measured at five locations and the thickness of release liner/backing membrane was measured at three locations. Average film thickness was determined by subtracting the mean release liner/backing membrane thickness from the mean patch thickness Drug in adhesive mixtures for adhesive Duro-Tak® 87-2677 required the addition of isopropyl alcohol (1 g before the addition of 4 g adhesive) prior to casting to reduce mixture viscosity and aid solvation. This additional solvent would be removed during drying.

Table 6 below provides an example of an adhesive wet casting mixture.

TABLE 6

Wet casting mixture - 4% ropivacaine in Duro-Tak ® 87-900A

| Component | Common name | Target wt (4 g adhesive batch) (g) | % w/w (wet basis) | % w/w (dry basis) |
|---|---|---|---|---|
| ropivacaine | ropivacaine base | 0.073 | 1.79 | 4.0 |
| Duro-tak 87-900A* | acrylate-vinylacetate pressure sensitive adhesive | 4.00 | 98.21 | 96.0 |

*based on 43.88% solids (% solids will vary between batches of adhesive)

Duro-Tak® 87-2677 and Duro-Tak® 87-900A demonstrated compatibility with release liner 3M 9741 (fluoropolymer coated polypropylene film). Duro-Tak® 87-2074 demonstrated compatibility with release liner 3M 1022 (fluoropolymer coated polypropylene film).

A range of ropivacaine in adhesive patches prepared according the above protocol are provided in Table 7 below:

TABLE 7

Ropivacaine (API) in adhesive transdermal patch compositions

| Example | % API | Adhesive | Release liner | Backing |
|---|---|---|---|---|
| 1 | 3 | 87-900A | 9741 | 9730 |
| 2 | 4 | 87-900A | 9741 | 9730 |
| 3 | 5* | 87-900A | 9741 | 9730 |
| 4 | 5 | 87-2074 | 1022 | 9730 |
| 5 | 7.5 | 87-2074 | 1022 | 9730 |
| 6 | 10 | 87-2074 | 1022 | 9730 |
| 7 | 12 | 87-2074 | 1022 | 9730 |
| 8 | 5 | 87-2677 | 9741 | 9730 |
| 9 | 7.5 | 87-2677 | 9741 | 9730 |
| 10 | 10* | 87-2677 | 9741 | 9730 |

*drug precipitation observed hence patch above saturation

Adhesive Plus One or More Excipients

All formulations were prepared with 4 g of adhesive. The loadings of other constituents (prepared as w/w), such as excipients, were adjusted for percentage solids of adhesive, such that the patch loadings were relative to the dry adhesive weight.

Ropivacaine was weighed into a single vessel. The one or more excipients were added followed by the adhesive, and the vessel was capped. Isopropyl alcohol was added before the addition of the adhesive for preparations using Duro-Tak® 87-2677. The vessel contents were then mixed using a roller mixer until a homogeneous mixture was obtained, and the ropivacaine was fully dissolved. Casting thicknesses were adjusted to account for the inclusion of the excipient mixture where appropriate. The mixtures were cast, dried and laminated according to the protocols described for adhesive only formulations.

A transdermal patch containing 7.5% (w/w) ropivacaine and 5% (w/w) Transcutol® was successfully prepared according to the above protocol using Duro-Talc® adhesive 87-2677, 3M 9741 release liner and 3M 9730 occlusive backing membrane.

Table 8, below, provides a range of other transdermal patches prepared according to the above protocol, each containing a single excipient.

TABLE 8

Ropivacaine (API) in transdermal patches containing adhesive and 1 excipient

| Example | % API | Excipient | % Excipient | Adhesive | Release liner | Backing membrane |
|---|---|---|---|---|---|---|
| 11 | 4 | Transcutol P | 5 | 87-900A | 3M 9741 | 3M 9730 |
| 12 | 4 | Labrafac PG | 5 | 87-900A | 3M 9741 | 3M 9730 |
| 13 | 4 | Capryol 90 | 5 | 87-900A | 3M 9741 | 3M 9730 |
| 14 | 4 | Captex 355 | 5 | 87-900A | 3M 9741 | 3M 9730 |

A binary excipient mixture containing propylene glycol and Brij® 93 demonstrated good compatibility with Duro-Tak® adhesive 87-900A. A patch containing 10% propylene glycol, 2% (w/w) Brij® 93 and 4% ropivacaine was prepared.

Transdermal patches containing a ternary mixture of excipients were prepared according to the above protocol. Table 9, below, provides an example of a wet casting mixture containing an adhesive and a ternary excipient mixture:

TABLE 9

Wet casting mixture - 6.5% (w/w) ropivacaine, 35% (w/w) [30/60/10] propylene glycol/Capryol ®90/Brij ®93 in Duro-Tak ® 87-2677

| Component | Common name | Target wt (4 g adhesive batch) g) | % w/w (wet basis) | % w/w (dry basis) |
|---|---|---|---|---|
| ropivacaine | ropivacaine base | 0.1729 | 2.84 | 6.5 |
| propylene glycol | 1,2 propandiol | 0.2777 | 4.55 | 10.5 |
| Capryol 90 | propylene glycol monocaprylate type II | 0.5554 | 9.11 | 21.0 |
| Brij 93 | Polyoxyethylene (2) oleyl ether | 0.0926 | 1.52 | 3.5 |
| IPA | 2-propanol | 1.00 | 16.4 | — |
| Duro-tak 87-2677* | acrylate-vinylacetate pressure sensitive adhesive | 4.00 | 65.6 | 58.5 |

*based on 38.68% solids (% solids will vary between batches of adhesive)

Further transdermal patch formulations containing adhesive and a ternary mixture of excipients were prepared, as shown in Table 9 below:

TABLE 9

Ropivacaine (API) in transdermal patches containing adhesive and a ternary mixture of excipients

| Example | % API | Adhesive | % [30/60/10] (PG/Capryol 90/Brij 93) | Release liner | Backing |
|---|---|---|---|---|---|
| 15 | 4 | 87-900A | 15 | 3M 9741 | 3M 9730 |
| 16 | 7.5 | 87-2677 | 15 | 3M 9741 | 3M 9730 |
| 17 | 11 | 87-2074 | 15 | 3M 1022 | 3M 9730 |
| 18 | 12 | 87-2074 | 15 | 3M 1022 | 3M 9730 |

Transdermal patches containing other ternary or quaternary mixtures of excipients were also prepared according to the above protocol, see Tables 10 and 11 below:

TABLE 10

Ropivacaine (API) in transdermal patches containing adhesive and a ternary or quaternary mixture of excipients

| Example | % API | Excipient mixture* | Total excipient loading (%) | Adhesive | Release liner | Backing membrane |
|---|---|---|---|---|---|---|
| 19 | 7.5 | 1 | 15 | 87-2677 | 3M 9741 | 3M 9730 |
| 20 | 7.5 | 2 | 15 | 87-2677 | 3M 9741 | 3M 9730 |
| 21 | 7.5 | 3 | 15 | 87-2677 | 3M 9741 | 3M 9730 |
| 22 | 7.5 | 5 | 15 | 87-2677 | 3M 9741 | 3M 9730 |
| 23 | 7.5 | 6 | 15 | 87-2677 | 3M 9741 | 3M 9730 |
| 24 | 7.5 | 8 | 15 | 87-2677 | 3M 9741 | 3M 9730 |
| 25 | 7.5 | 9 | 15 | 87-2677 | 3M 9741 | 3M 9730 |

*excipient mixture identified in Table 5

TABLE 11

Ropivacaine (API) in transdermal patches containing adhesive and a ternary or quaternary mixture of excipients

| Example | % API | Excipient component | Adhesive | Release liner | Backing | Thick (μm) |
|---|---|---|---|---|---|---|
| 26 | 6.5 | 35% [30/60/10] (PG/cap 90/Brij93) | 87-2677 | 3M 9741 | 3M 9730 | ~92 |
| 27 | 6.5 | 35% [30/60/10] (HG/cap 90/Brij93) | 87-2677 | 3M 9741 | 3M 9730 | ~83 |
| 28 | 6.5 | 5% Transcutol, 20% [30/60/10] (PG/cap 90/Brij93) | 87-2677 | 3M 9741 | 3M 9730 | ~84 |

EVA Membrane Release Studies

Release studies were performed for selected transdermal patches and saturated aqueous solutions. For transdermal patches, circular (10 mm diameter) samples were punched out and applied to 3M 9702 CoTran® membranes (9% EVA) mounted in horizontal Franz-type diffusion cells. Saturated aqueous solutions were prepared at 32° C. (mixing time ≥18-24 hours). To avoid donor phase depletion, excess ropivacaine was added to the saturated solution when applied (1 ml) to 3M 9702 CoTran® membranes (9% EVA)

and donor chambers were occluded. The receptor medium used was Walpole's acetate buffer pH4. The cells were immersed in a thermostatically controlled water bath at 32° C.±0.5° C. and the receptor phase was continually agitated with a magnetic follower. Permeation of ropivacaine and lidocaine through the EVA membrane was measured at eight intervals over 48 hours (typically at 1, 2, 4, 6, 8. 12. 24 and 48 hours from dosing). Each sample was placed into a pre-labelled 200 µl glass vial (gold grade, Chromacol®) and a PTFE cap was applied. If analysis could not be performed immediately, samples were frozen at −20° C. pending analysis. The liquid removed in each sample was replaced with fresh, temperature-equilibrated blank receptor medium. Samples of the receptor phase were analysed for ropivacaine by HPLC and the permeated amounts were calculated ($\mu g/cm^2$).

Suitable calibration plots were constructed using standard solutions prepared in Walpole's acetate buffer pH 4. The five level calibrations ranged from 0.1 to 50 µg/ml ropivacaine or lidocaine. The limit of quantitation (LOQ) was the area for calibration level 1 (0.1 µg/ml) and any result below the LOQ was classed as a zero result. A quality assurance (QA) sample (calibration level 4, 10 µg/ml) was included in each analytical run.

Adhesive Only Patches

FIG. 1 compares the permeation, over 48 hours, of ropivacaine from the transdermal patch formulation provided in Table 7, together with a ropivacaine saturated aqueous solution and a ropivacaine saturated citrate acetate buffer solution at pH 5, using a 9% EVA ((3M 9702) membrane.

Adhesive Plus One or More Excipients

FIG. 2 suggests that the permeation rate of ropivacaine from a 4% (w/w) ropivacaine in Duro-Tak® 87-900A is greater than that from a 7.5% (w/w) ropivacaine in Duro-Tak® 87-2677 patch containing 5% (w/w) Transcutol®.

FIG. 3 compares the permeation, over 48 hours, of ropivacaine from a simple ropivacaine-in-adhesive (Duro-Tak® 87-2677) patch, with one containing 15% (w/w) of a ternary propylene glycol, Capryol® 90, Brij® 93 (30/60/10) excipient mixture. Improved permeation is observed for the patch containing the ternary excipient mixture.

FIG. 4 compares the permeation, over 48 hours, of ropivacaine from selected transdermal patch formulations provided in Table 10, containing 15% (w/w) of ternary/quaternary excipient mixtures. All tested patches demonstrated similar permeation characteristics.

FIG. 5 compares the permeation, over 48 hours, of ropivacaine from selected transdermal patch formulations provided in Table 11, with a transdermal patch containing an increased quantity of ropivacaine. The results demonstrate that for patches having an increased quantity of excipient mixture, improved permeation can be achieved using reduced quantities of dissolved ropivacaine.

In Vitro Human Skin Permeation Studies

In vitro human skin permeation studies were performed for selected transdermal patches and saturated aqueous solutions. For patches, circular (10 mm diameter) samples were punched out and applied to human epidermal membranes (surgical excess abdominal tissue from 3 donors, n=6) mounted in horizontal Franz-type diffusion cells. Saturated aqueous solutions were prepared at 32° C. (mixing time ≥18-24 hours). To avoid donor phase depletion, excess ropivacaine or lidocaine was added to the saturated solution when applied (1 ml) to skin in vitro. Donor chambers were occluded. The receptor medium was 25/75 (v/v) ethanol/pH 7.4 phosphate buffered saline (EPBS) and provided sink conditions for the test permeants (<10% saturated). Skin surface temperature was maintained at 32° C.±1° C. by immersing the cells in a thermostatically controlled water bath (at 37° C.±0.5° C.). The receptor medium was continually stirred with a magnetic follower. Permeation of ropivacaine through the skin membrane was measured at five time-points over 24 hours. Samples of the receptor phase were analysed for active by HPLC and the permeated amounts ($\mu g/cm^2$) and the mid time-point flux (rate of delivery, $\mu g/cm^2/h$) were calculated. Mean±standard error (SE) data are presented.

Separation was performed on a C18, 4 µm, 150×4.6 mm HPLC column. An isocratic method was used and the mobile phase was 35/65 (v/v) acetonitrile/$H_2O$ plus 10 mM sodium heptane sulfonate and 0.1% acetic acid. The flow rate was 1 ml/min and the runtime 10 minutes per sample. A 20 µl full loop injection was used for all samples and the column oven temperature was 35° C. Discrete wavelengths were collected at 224 nm ($\lambda_m$ and wavelength used for quantitation) and 263 nm plus UV scan data 210-310 nm were collected for peak identification purposes. The retention time for ropivacaine was ~7.0 minutes and ~4.6 minutes for lidocaine. Where required, samples were diluted into the calibration range (0.1-50 µg/ml).

Adhesive Only Patches

FIG. 6 demonstrates the poor in vitro human skin permeation properties of a saturated ropivacaine solution versus those of a saturated lidocaine solution (both solutions contained excess solid).

FIG. 7 compares the in vitro human skin permeation, over 48 hours, of ropivacaine from a patch containing 7.5% (w/w) ropivacaine in Duro-Tak® 87-2677 adhesive, with a simple ropivacaine-saturated solution (plus excess solid). The effect of removing the patch after 24 hours is clearly shown (release of approximately 4 $\mu g/cm^2$ from the skin over the subsequent 24 hours).

FIG. 8 demonstrates the in vitro human skin permeation, over 24 hours, of ropivacaine from a patch containing 4% (w/w) ropivacaine in Duro-Tak® 87-900A adhesive. Comparison of this data with that of a 7.5% (w/w) ropivacaine in Duro-Tak® 87-2677 adhesive showed similar in vitro human skin permeation characteristics for both patches.

FIG. 9 demonstrates the mid time-point flux ($\mu g/cm^2\ h^{-1}$) for a 4% (w/w) ropivacaine in Duro-Tak® 87-900A transdermal patch.

Adhesive Plus One or More Excipients

Table 12, below, provides the in vitro human skin permeation values, over 24 hours, of ropivacaine from a patch containing 7.5% (w/w) ropivacaine in Duro-Talc® 87-2677 adhesive, with an identical patch containing 15% (w/w) of a ternary propylene glycol, Capryol® 90, Brij® 93 (30/60/10) excipient mixture. Permeation values for a 4% (w/w) ropivacaine in Duro-Tak® 87-900A adhesive are also provided.

TABLE 12

Ropivacaine in vitro human skin permeation from adhesive only and ternary excipient mixture patches

| | $\mu g/cm^2$ (mean ± SE) | | |
|---|---|---|---|
| Time point (h) | 7.5% ropiv, 15% [30/60/10] (PG/Cap 90/Brij 93) in 2677 (Example 16) | 7.5% ropivacaine in 2677 (Example 9) | 4% ropivacaine in 900A (Example 2) |
| 3 | 2.65 ± 0.43 | — | 3.92 ± 1.22 |
| 6 | 12.1 ± 1.9 | 9.74 ± 1.29 | 14.0 ± 3.1 |
| 9 | 23.1 ± 3.1 | — | 23.7 ± 4.3 |
| 12 | 34.1 ± 4.0 | 27.2 ± 2.2 | 32.7 ± 5.1 |
| 24 | 75.5 ± 6.7 | 59.8 ± 2.8 | 63.6 ± 7.9 |

Referring to Table 12, FIG. 10 compares the in vitro human skin permeation, over 24 hours, of ropivacaine from a patch containing 7.5% (w/w) ropivacaine in Duro-Talc® 87-2677 adhesive, with an identical patch containing 15% (w/w) of a ternary propylene glycol, Capryol® 90, Brij® 93 (30/60/10) excipient mixture. Improved in vitro human skin permeation is observed for the patch containing the ternary excipient mixture.

Referring to Table 12, FIG. 11 demonstrates the mid time-point flux ($\mu g/cm^2\ h^{-1}$) for a transdermal patch containing 7.5% (w/w) ropivacaine and 15% (w/w) of a ternary propylene glycol, Capryol® 90, Brij® 93 (30/60/10) excipient mixture in Duro-Tak® 87-2677 adhesive.

Table 13, below, provides the in vitro human skin permeation values, over 24 hours, of ropivacaine from patches containing ternary and quaternary excipient mixtures, with a commercially available lidocaine transdermal patch (Versatis).

TABLE 13

In vitro human skin permeation from ropivacaine and lignocaine transdermal patches

| | $\mu g/cm^2$ (mean ± SE) | | |
|---|---|---|---|
| Time point (h) | 6.5% ropiv, 35% [30/60/10] (PG/Cap 90/Brij 93) in 2677 (Example 26) | 6.5% ropiv, 5% menthol, 20% [30/60/10] (PG/Cap 90/Brij 93) in 2677 (Example 29) | 5% lidocaine, Versatis (Comparative example 1) |
| 3 | 6.07 ± 1.68 | 3.56 ± 0.66 | 5.33 ± 1.23 |
| 6 | 17.5 ± 3.2 | 12.7 ± 1.5 | 14.7 ± 1.9 |
| 9 | 29.8 ± 4.5 | 22.2 ± 2.2 | 28.2 ± 2.4 |
| 12 | 43.8 ± 5.1 | 31.3 ± 2.9 | 45.4 ± 3.8 |
| 24 | 91.9 ± 9.0 | 63.4 ± 5.0 | 127.6 ± 6.9 |

Referring to Table 13, FIG. 12 compares the in vitro human skin permeation, over 24 hours, of ropivacaine from certain transdermal patches containing ternary or quaternary excipient mixtures, with a commercially-available lignocaine transdermal patch (Verstatis).

Referring to Table 13, FIG. 13 compares the mid time-point flux ($\mu g/cm^2\ h^{-1}$) for certain transdermal patches containing ternary or quaternary excipient mixtures, and a commercially-available lignocaine transdermal patch (Verstatis).

Table 14, below, provides the in vitro human skin apparent steady state flux values for ropivacaine, over either 3-12 or 4-12 hours, from patches containing either drug in adhesive alone or with ternary and quaternary excipient mixtures. Flux values for ropivacaine and lidocaine saturated aqueous solutions are also provided. Flux values were calculated using a linear fit of the permeation data (as presented in FIGS. 7, 8, 10 and 12) during apparent steady-state delivery and correlation coefficients are provided ($r^2 \geq 0.998$ throughout).

TABLE 14

In vitro human skin apparent steady-state flux values from ropivacaine transdermal patches, and ropivacaine and lignocaine saturated aqueous solutions

| Run | Time range (h) | Calculated flux ($\mu g \cdot cm^{-2} \cdot h^{-1}$) | Correlation coefficient, $r^2$ |
|---|---|---|---|
| 7.5% Ropivacaine in 87-2677 (Example 9) | 4-12 | 2.87 | 1.000 |
| Ropivacaine saturated H2O | 4-12 | 2.52 | 1.000 |
| Lidocaine saturated H2O | 4-12 | 70.7 | 0.999 |
| 4% ropivacaine in 87-900A Example 2) | 3-12 | 3.20 | 0.999 |
| 7.5% Ropivacaine, 15% [30/60/10] (PG/Cap 90/Brij 93) in 87-2677 (Example 16) | 3-12 | 3.51 | 0.999 |
| 6.5% Ropivacaine, 35% [30/60/10] (PG/Cap 90/Brij 93) in 87-2677 (Example 26) | 3-12 | 4.19 | 0.998 |
| 6.5% Ropivacaine, 5% menthol, 20% [30/60/10] (PG/Cap 90/Brij 93) in 87-2677 (Example 29) | 3-12 | 3.09 | 1.000 |

What is claimed is:

1. A transdermal patch comprising a pharmaceutical formulation, said formulation comprising:
   (i) ropivacaine,
   (ii) a pharmaceutically-acceptable adhesive, and
   (iii) two or three excipients selected from a penetration enhancer, a hydrophilic material, and a carrier oil having a ropivacaine solubility of greater than or equal to 1.5% (w/w);
   wherein said ropivacaine is present in its free base form and wherein said patch further comprises a backing membrane.

2. A transdermal patch as claimed in claim 1, wherein the pharmaceutical formulation has an in vitro human skin permeation rate of the ropivacaine that is greater than 1.8 $\mu g\ cm^{-2}\ h^{-1}$.

3. A transdermal patch as claimed in claim 1, wherein the pharmaceutical formulation has an in vitro human skin permeation rate of the ropivacaine that is between 1.8 $\mu g\ cm^{-2}\ h^{-1}$ and 10 $\mu g\ cm^{-2}\ h^{-1}$.

4. A transdermal patch as claimed in claim 1, wherein amount of the ropivacaine is between 3 and 20% w/w.

5. A transdermal patch as claimed in claim 1, wherein the adhesive has a ropivacaine solubility greater than 2.5% w/w at room temperature.

6. A transdermal patch as claimed in claim 1, wherein the amount of adhesive is between 58 and 97% w/w.

7. A transdermal patch as claimed in claim 1, wherein the adhesive is selected from acrylate/polyacrylate materials, rubbers or silicones.

8. A transdermal patch as claimed in claim 1, wherein the adhesive is an acrylate copolymer material or an acrylate-vinylacetate material.

9. A transdermal patch as claimed in claim 1, further comprising a carrier oil in an amount of between 2.5 and 35% w/w.

10. A transdermal patch as claimed in claim 9, wherein the carrier oil has a water solubility of less than 0.1% w/w and a ropivacaine solubility in excess of 3% w/w.

11. A transdermal patch as claimed in claim 9, wherein the carrier oil is selected from the group consisting of sorbitan monooleate, sorbitan trioleate, triglycerides of carprylic/capric acid, propylene glycol dicaprylate/dicaprate, ethoxy diglycol, propylene glycol monocaprylate, glycerol monooleate, lanolin, acetylated lanolin, polyethylene glycol lanolin, glycerol monocaprylate/caprate, propylene glycol laurate, and/or mono- or diglycerides of capric acid.

12. A transdermal patch as claimed in claim 1, further comprising a penetration enhancer in an amount of between 1.4 and 15% w/w.

13. A transdermal patch as claimed in claim 12, wherein the penetration enhancer is selected from the group consisting of sugar fatty acid esters and ethers, $C_8$-$C_{18}$ fatty alcohol, azone, oleic ethers, terpenes and ethoxy ethanols.

14. A transdermal patch as claimed in claim 1, further comprising a hydrophilic material in an amount of between 1.5 and 20% w/w.

15. A transdermal patch as claimed in claim 14, wherein the hydrophilic material is selected from the group consisting of propylene glycol, glycerol, polyethylene glycol, short chain water soluble esters of citric acid, acetic acid, hexylene glycol and alcohols, including diols and polyols.

16. A transdermal patch as claimed in claim 1, comprising propylene glycol monocaprylate, propylene glycol and polyoxyethylene oleyl ether present as a ternary mixture in an amount of between 10 and 40% w/w.

17. A transdermal patch as claimed in claim 16, wherein the ternary mixture further comprises an additive selected from the group consisting of non-ionic surfactants, hydrophilic surfactants, terpenes and membrane disruptors.

18. A transdermal patch as claimed in claim 1, wherein the formulation comprises a penetration enhancer, a hydrophilic material and a carrier oil having a ropivacaine solubility of greater than or equal to 1.5% (w/w).

19. A transdermal patch as claimed in claim 18 wherein the quantity of (iii) present in the formulation is from 10% (w/w) to about 40% (w/w).

* * * * *